US011970697B2

(12) United States Patent
Lackey et al.

(10) Patent No.: US 11,970,697 B2
(45) Date of Patent: Apr. 30, 2024

(54) METHODS OF SYNTHESIZING OLIGONUCLEOTIDES USING TETHERED NUCLEOTIDES

(71) Applicant: Twist Bioscience Corporation, South San Francisco, CA (US)

(72) Inventors: Jeremy Lackey, Foster City, CA (US); David Dodd, San Francisco, CA (US)

(73) Assignee: Twist Bioscience Corporation, South San Franciso (CA)

( * ) Notice: Subject to any disclaimer, the term of this patent is extended or adjusted under 35 U.S.C. 154(b) by 0 days.

(21) Appl. No.: 17/504,358

(22) Filed: Oct. 18, 2021

(65) Prior Publication Data
US 2022/0145289 A1 May 12, 2022

Related U.S. Application Data

(60) Provisional application No. 63/093,716, filed on Oct. 19, 2020.

(51) Int. Cl.
*C12N 15/10* (2006.01)
*C12N 15/113* (2010.01)

(52) U.S. Cl.
CPC ....... *C12N 15/1093* (2013.01); *C12N 15/102* (2013.01); *C12N 15/113* (2013.01); *C12N 2310/315* (2013.01); *C12N 2320/33* (2013.01)

(58) Field of Classification Search
CPC .............. C12N 15/1093; C12N 15/102; C12N 15/113; C12N 2310/315; C12N 2320/33; C12Y 207/07031
See application file for complete search history.

(56) References Cited

U.S. PATENT DOCUMENTS

| 5,368,823 | A | 11/1994 | McGraw et al. |
| 5,474,796 | A | 12/1995 | Brennan |
| 5,534,507 | A | 7/1996 | Cama et al. |
| 5,677,195 | A | 10/1997 | Winkler et al. |
| 5,843,767 | A | 12/1998 | Beattie |
| 6,013,440 | A | 1/2000 | Lipshutz et al. |
| 6,028,189 | A | 2/2000 | Blanchard |
| 6,419,883 | B1 | 7/2002 | Blanchard |
| 6,472,147 | B1 | 10/2002 | Janda et al. |
| 6,492,107 | B1 | 12/2002 | Kauffman et al. |

(Continued)

FOREIGN PATENT DOCUMENTS

| CN | 101277758 A | 10/2008 |
| EP | 3030682 A2 | 6/2016 |

(Continued)

OTHER PUBLICATIONS

Agbavwe et al.: Efficiency, Error and Yield in Light-Directed Maskless Synthesis of DNA Microarrays. Journal of Nanobiotechnology. 9(57):1-17 (2011).

(Continued)

*Primary Examiner* — Jeremy C Flinders
(74) *Attorney, Agent, or Firm* — Bookoff McAndrews, PLLC

(57) ABSTRACT

Disclosed herein are methods and compositions comprising a polymerase and a phosphorylated nucleoside, wherein the polymerase and the nucleoside are covalently linked by a cleavable linker at the terminal phosphate group. Further disclosed herein are enzymatic polynucleotide synthesis using polymerase and nucleotide conjugation strategies.

20 Claims, 21 Drawing Sheets

(56) References Cited

U.S. PATENT DOCUMENTS

| | | |
|---|---|---|
| 6,893,816 B1 | 5/2005 | Beattie |
| 7,163,660 B2 | 1/2007 | Lehmann |
| 7,202,264 B2 | 4/2007 | Ravikumar et al. |
| 8,198,071 B2 | 6/2012 | Goshoo et al. |
| 9,403,141 B2 | 8/2016 | Banyai et al. |
| 9,409,139 B2 | 8/2016 | Banyai et al. |
| 9,555,388 B2 | 1/2017 | Banyai et al. |
| 9,677,067 B2 | 6/2017 | Toro et al. |
| 9,745,619 B2 | 8/2017 | Rabbani et al. |
| 9,765,387 B2 | 9/2017 | Rabbani et al. |
| 9,833,761 B2 | 12/2017 | Banyai et al. |
| 9,839,894 B2 | 12/2017 | Banyai et al. |
| 9,889,423 B2 | 2/2018 | Banyai et al. |
| 9,895,673 B2 | 2/2018 | Peck et al. |
| 9,981,239 B2 | 5/2018 | Banyai et al. |
| 10,053,688 B2 | 8/2018 | Cox |
| 10,272,410 B2 | 4/2019 | Banyai et al. |
| 10,384,188 B2 | 8/2019 | Banyai et al. |
| 10,384,189 B2 | 8/2019 | Peck |
| 10,417,457 B2 | 9/2019 | Peck |
| 10,583,415 B2 | 3/2020 | Banyai et al. |
| 10,618,024 B2 | 4/2020 | Banyai et al. |
| 10,632,445 B2 | 4/2020 | Banyai et al. |
| 10,639,609 B2 | 5/2020 | Banyai et al. |
| 10,669,304 B2 | 6/2020 | Indermuhle et al. |
| 10,744,477 B2 | 8/2020 | Banyai et al. |
| 10,754,994 B2 | 8/2020 | Peck |
| 10,773,232 B2 | 9/2020 | Banyai et al. |
| 10,844,373 B2 | 11/2020 | Cox et al. |
| 10,894,242 B2 | 1/2021 | Marsh et al. |
| 10,894,959 B2 | 1/2021 | Cox et al. |
| 10,907,274 B2 | 2/2021 | Cox |
| 10,936,953 B2 | 3/2021 | Bramlett et al. |
| 10,969,965 B2 | 4/2021 | Malina et al. |
| 10,975,372 B2 | 4/2021 | Cox et al. |
| 10,987,648 B2 | 4/2021 | Peck et al. |
| 11,214,798 B2 | 1/2022 | Brown |
| 11,562,103 B2 | 1/2023 | Peck |
| 2001/0018512 A1 | 8/2001 | Blanchard |
| 2002/0025561 A1 | 2/2002 | Hodgson |
| 2002/0094533 A1 | 7/2002 | Hess et al. |
| 2002/0095073 A1 | 7/2002 | Jacobs et al. |
| 2002/0160536 A1 | 10/2002 | Regnier et al. |
| 2002/0164824 A1 | 11/2002 | Xiao et al. |
| 2003/0120035 A1 | 6/2003 | Gao et al. |
| 2003/0171325 A1 | 9/2003 | Gascoyne et al. |
| 2004/0087008 A1 | 5/2004 | Schembri |
| 2004/0259146 A1 | 12/2004 | Friend et al. |
| 2005/0137805 A1 | 6/2005 | Lewin et al. |
| 2005/0227235 A1 | 10/2005 | Carr et al. |
| 2006/0127920 A1 | 6/2006 | Church et al. |
| 2007/0196834 A1 | 8/2007 | Cerrina et al. |
| 2008/0085511 A1 | 4/2008 | Peck et al. |
| 2008/0085514 A1 | 4/2008 | Peck et al. |
| 2008/0227160 A1 | 9/2008 | Kool |
| 2008/0287320 A1 | 11/2008 | Baynes et al. |
| 2008/0300842 A1 | 12/2008 | Govindarajan et al. |
| 2009/0062129 A1 | 3/2009 | McKernan et al. |
| 2009/0239759 A1 | 9/2009 | Balch |
| 2009/0285825 A1 | 11/2009 | Kini et al. |
| 2010/0004143 A1 | 1/2010 | Shibahara |
| 2010/0099103 A1 | 4/2010 | Hsieh et al. |
| 2010/0111768 A1 | 5/2010 | Banerjee et al. |
| 2010/0216648 A1 | 8/2010 | Staehler et al. |
| 2010/0311960 A1 | 12/2010 | Dellinger |
| 2011/0172127 A1 | 7/2011 | Jacobson et al. |
| 2011/0217738 A1 | 9/2011 | Jacobson |
| 2012/0129704 A1 | 5/2012 | Gunderson et al. |
| 2012/0164691 A1 | 6/2012 | Eshoo et al. |
| 2012/0231968 A1 | 9/2012 | Bruhn et al. |
| 2012/0264653 A1 | 10/2012 | Carr et al. |
| 2013/0017642 A1 | 1/2013 | Milgrew et al. |
| 2013/0017977 A1 | 1/2013 | Oleinikov |
| 2013/0065017 A1 | 3/2013 | Sieber |
| 2013/0109595 A1 | 5/2013 | Routenberg |
| 2013/0109596 A1 | 5/2013 | Peterson et al. |
| 2013/0130321 A1 | 5/2013 | Staehler et al. |
| 2013/0165328 A1 | 6/2013 | Previte et al. |
| 2014/0106394 A1 | 4/2014 | Ko et al. |
| 2014/0178992 A1 | 6/2014 | Nakashima et al. |
| 2015/0038373 A1 | 2/2015 | Banyai et al. |
| 2015/0120265 A1 | 4/2015 | Amirav-Drory et al. |
| 2015/0196917 A1 | 7/2015 | Kay et al. |
| 2016/0089651 A1 | 3/2016 | Banyai |
| 2016/0090592 A1 | 3/2016 | Banyai et al. |
| 2016/0096160 A1 | 4/2016 | Banyai et al. |
| 2016/0251651 A1 | 9/2016 | Banyai et al. |
| 2016/0303535 A1 | 10/2016 | Banyai et al. |
| 2016/0333340 A1 | 11/2016 | Wu |
| 2016/0339409 A1 | 11/2016 | Banyai et al. |
| 2016/0340672 A1 | 11/2016 | Banyai et al. |
| 2016/0354752 A1 | 12/2016 | Banyai et al. |
| 2017/0081716 A1 | 3/2017 | Peck |
| 2017/0095785 A1 | 4/2017 | Banyai et al. |
| 2017/0159044 A1 | 6/2017 | Toro et al. |
| 2017/0327819 A1 | 11/2017 | Banyai et al. |
| 2017/0357752 A1 | 12/2017 | Diggans |
| 2017/0362589 A1 | 12/2017 | Banyai et al. |
| 2018/0029001 A1 | 2/2018 | Banyai et al. |
| 2018/0104664 A1 | 4/2018 | Fernandez |
| 2018/0142289 A1 | 5/2018 | Zeitoun et al. |
| 2018/0253563 A1 | 9/2018 | Peck et al. |
| 2018/0264428 A1 | 9/2018 | Banyai et al. |
| 2018/0282721 A1 | 10/2018 | Cox et al. |
| 2018/0326388 A1 | 11/2018 | Banyai et al. |
| 2019/0112627 A1 | 4/2019 | Arlow et al. |
| 2019/0135926 A1 | 5/2019 | Glanville |
| 2019/0314783 A1 | 10/2019 | Banyai et al. |
| 2019/0352635 A1 | 11/2019 | Toro et al. |
| 2019/0366293 A1 | 12/2019 | Banyai et al. |
| 2019/0366294 A1 | 12/2019 | Banyai et al. |
| 2020/0017907 A1 | 1/2020 | Zeitoun et al. |
| 2020/0102611 A1 | 4/2020 | Zeitoun et al. |
| 2020/0156037 A1 | 5/2020 | Banyai et al. |
| 2020/0181667 A1 | 6/2020 | Wu et al. |
| 2020/0199662 A1 | 6/2020 | Strauss et al. |
| 2020/0222875 A1 | 7/2020 | Peck et al. |
| 2020/0283760 A1 | 9/2020 | Nugent et al. |
| 2020/0299322 A1 | 9/2020 | Indermuhle et al. |
| 2020/0299684 A1 | 9/2020 | Toro et al. |
| 2020/0308575 A1 | 10/2020 | Sato |
| 2020/0325235 A1 | 10/2020 | Tabibiazar et al. |
| 2020/0330953 A1 | 10/2020 | Banyai et al. |
| 2020/0342143 A1 | 10/2020 | Peck |
| 2021/0002710 A1 | 1/2021 | Gantt et al. |
| 2021/0040476 A1 | 2/2021 | Cox et al. |
| 2021/0071168 A1 | 3/2021 | Nugent et al. |
| 2021/0102192 A1 | 4/2021 | Tabibiazar et al. |
| 2021/0102195 A1 | 4/2021 | Sato et al. |
| 2021/0102198 A1 | 4/2021 | Cox et al. |
| 2021/0115594 A1 | 4/2021 | Cox et al. |
| 2021/0129108 A1 | 5/2021 | Marsh et al. |
| 2021/0142182 A1 | 5/2021 | Bramlett et al. |
| 2021/0170356 A1 | 6/2021 | Peck et al. |
| 2021/0179724 A1 | 6/2021 | Sato et al. |
| 2021/0180046 A1 | 6/2021 | Cox et al. |
| 2021/0207197 A1 | 7/2021 | Gantt et al. |
| 2021/0332078 A1 | 10/2021 | Wu |
| 2021/0348220 A1 | 11/2021 | Zeitoun et al. |
| 2021/0355194 A1 | 11/2021 | Sato et al. |
| 2021/0395344 A1 | 12/2021 | Sato et al. |
| 2022/0032256 A1 | 2/2022 | Lackey et al. |
| 2022/0064206 A1 | 3/2022 | Fernandez et al. |
| 2022/0064313 A1 | 3/2022 | Sato et al. |
| 2022/0064628 A1 | 3/2022 | Toro et al. |
| 2022/0106586 A1 | 4/2022 | Nugent et al. |
| 2022/0106590 A1 | 4/2022 | Arbiza et al. |
| 2022/0135690 A1 | 5/2022 | Sato et al. |
| 2022/0135965 A1 | 5/2022 | Gantt et al. |
| 2022/0206001 A1 | 6/2022 | Sato |
| 2022/0243195 A1 | 8/2022 | Nugent et al. |
| 2022/0246236 A1 | 8/2022 | Amirav-Drory |
| 2022/0259319 A1 | 8/2022 | Sato et al. |
| 2022/0259638 A1 | 8/2022 | Brown |

(56) References Cited

U.S. PATENT DOCUMENTS

| | | | |
|---|---|---|---|
| 2022/0277808 | A1 | 9/2022 | Arbiza et al. |
| 2022/0281989 | A1 | 9/2022 | Glanville |
| 2022/0307010 | A1 | 9/2022 | Sato et al. |
| 2022/0315971 | A1 | 10/2022 | Wu et al. |
| 2022/0323924 | A1 | 10/2022 | Lackey et al. |
| 2022/0325276 | A2 | 10/2022 | Banyai et al. |
| 2022/0325278 | A1 | 10/2022 | Nugent et al. |
| 2022/0348659 | A1 | 11/2022 | Sato et al. |
| 2022/0356463 | A1 | 11/2022 | Shen et al. |
| 2022/0356468 | A1 | 11/2022 | Sato et al. |
| 2022/0411784 | A1 | 12/2022 | Sato et al. |
| 2023/0002478 | A1 | 1/2023 | Sato et al. |
| 2023/0054232 | A1 | 2/2023 | Peck |
| 2023/0086062 | A1 | 3/2023 | Banyai et al. |
| 2023/0096464 | A1 | 3/2023 | Sato |
| 2023/0115861 | A1 | 4/2023 | Nugent et al. |

FOREIGN PATENT DOCUMENTS

| | | | |
|---|---|---|---|
| JP | H07505530 A | | 6/1995 |
| JP | 2001518086 A | | 10/2001 |
| JP | 2002538790 A | | 11/2002 |
| JP | 2004268394 A | | 9/2004 |
| JP | 2006503586 A | | 2/2006 |
| JP | 2007314746 A | | 12/2007 |
| JP | 2008214343 A | | 9/2008 |
| JP | 2009294195 A | | 12/2009 |
| JP | 2012507513 A | | 3/2012 |
| JP | 2016527313 A | | 9/2016 |
| WO | WO-9320242 | A1 | 10/1993 |
| WO | WO-02072791 | A2 | 9/2002 |
| WO | WO-2004039953 | A2 | 5/2004 |
| WO | WO-2005059096 | A2 | 6/2005 |
| WO | WO-2008054543 | A2 | 5/2008 |
| WO | WO-2008063135 | A1 | 5/2008 |
| WO | WO-2010053443 | A1 | 5/2010 |
| WO | WO-2011109031 | A1 | 9/2011 |
| WO | WO-2012078312 | A2 | 6/2012 |
| WO | WO-2012154201 | A1 | 11/2012 |
| WO | WO-2014021938 | A1 | 2/2014 |
| WO | WO-2015021080 | A2 | 2/2015 |
| WO | WO-2017223517 | A1 | 12/2017 |
| WO | WO-2022010934 | A2 | 1/2022 |
| WO | WO-2022076326 | A1 | 4/2022 |
| WO | WO-2022086866 | A1 | 4/2022 |
| WO | WO-2022087293 | A1 | 4/2022 |
| WO | WO-2022098662 | A2 | 5/2022 |
| WO | WO-2022159620 | A1 | 7/2022 |
| WO | WO-2022178137 | A1 | 8/2022 |
| WO | WO-2022204309 | A1 | 9/2022 |
| WO | WO-2022204316 | A2 | 9/2022 |
| WO | WO-2022217004 | A1 | 10/2022 |
| WO | WO-2022235579 | A1 | 11/2022 |
| WO | WO-2022235584 | A1 | 11/2022 |
| WO | WO-2022271884 | A2 | 12/2022 |
| WO | WO-2023023183 | A2 | 2/2023 |
| WO | WO-2023023190 | A2 | 2/2023 |
| WO | WO-2023023285 | A2 | 2/2023 |
| WO | WO-2023069367 | A1 | 4/2023 |

OTHER PUBLICATIONS

Palluk et al.: De novo DNA synthesis using polymerase-nucleotide conjugates. Nature Biotech. 36(7):645-650 (2018).
PCT/US2021/055454 Invitation to Pay Additional Fees dated Dec. 22, 2021.
U.S. Appl. No. 16/737,401 Office Action dated Jan. 5, 2022.
U.S. Appl. No. 16/737,401 Restriction Requirement dated Nov. 15, 2021.
Arkles et al.: The Role of Polarity in the Structure of Silanes Employed in Surface Modification. Silanes and Other Coupling Agents. 5:51-64 (2009).
ATDBio. Nucleic Acid Structure, Nucleic Acids Book, 9 pages, published on Jan. 22, 2005. from: http://www.atdbio.com/content/5/Nucleic-acid-structure.
ATDBio. Solid-Phase Oligonucleotide Synthesis, Nucleic Acids Book, 20 pages, Published on Jul. 31, 2011. from: http://www.atdbio.com/content/17/Solid-phase-oligonucleotide-synthesis.
Berg: Biochemistry. 5th ED. New York (2002) 148-149.
Blanchard et al.: High-Density Oligonucleotide Arrays. Biosensors & Bioelectronics, 11(6/7):687-690 (1996).
Buermans et al.: Next Generation sequencing technology: Advances and applications, Biochimica et Biophysica Acta (BBA)—Molecular Basis of Disease, 1842:1931-1941 (2014).
Cheng et al.: High throughput parallel synthesis of oligonucleotides with 1536 channel synthesizer. Nucleic Acids Res. 30(18):e93 (2002).
Cleary et al.: Production of complex nucleic acid libraries using highly parallel in situ oligonucleotide synthesis. Nat Methods. 1(3):241-248 (2004).
Cohen et al.: Human population: The next half century. Science. 302:1172-1175 (2003).
Cruse et al.: Atlas of Immunology. Third Edition. Boca Raton:CRC Press (pp. 282-283) (2010).
Elsik et al.: The Genome sequence of taurine cattle: A window of ruminant biology and evolution. Science. 324:522-528 (2009).
Fodor et al.: Light-directed, spatially addressable parallel chemical synthesis. Science. 251(4995):767-773 (1991).
Gao et al.: A method for the generation of combinatorial antibody libraries using pIX phage display. PNAS 99(20):12612-12616 (2002).
GE Healthcare. AKTA oligopilot plus. Data File 18-114-66 ADC. 8 pages (2006).
GE Healthcare. Robust and cost-efficient oligonucleotide synthesis. Application Note 28-4058-08 AA. 4 pages (2005).
Gibson et al.: Creation of a Bacterial Cell Controlled by a Chemically Synthesized Genome. Science. 329(5989):52-56 (2010).
Hudson: Matrix Assisted Synthetic Transformations: A Mosaic of Diverse Contributions. Journal of Combinatorial Chemistry. 1(6):403-457 (1999).
Kong et al.: Parallel gene synthesis in a microfluidic device. Nucleic Acids Res. 35(8):e61 (2007).
Kosuri and Church. Large-scale de novo DNA synthesis: technologies and applications. Nature Methods. 11:499-507 (2014) Available at: http://www.nature.com/nmeth/journal/v11/n5/full/nmeth.2918.html.
Kosuri, et al. A scalable gene synthesis by selective amplification of DNA pools from high-fidelity microchips. Nature Biotechnology. 2010; 28:1295-1299.
Kosuri et al.: A scalable gene synthesis platform using high-fidelity DNA microchips Nat.Biotechnol. 28(12):1295-1299 (2010).
Krayden, Inc.: A Guide to Silane Solutions. Silane coupling agents. 7 pages. Published on May 31, 2005 at: http://krayden.com/pdf/xia_silane_chemistry.pdf.
Lausted et al.: POSaM: a fast, flexible, open-source, inkjet oligonucleotide synthesizer and microarrayer. Genome Biology. 5:R58, 17 pages (2004) available at https://www.ncbi.nlm.nih.gov/pmc/articles/PMC507883/.
Lebl et al.: Economical Parallel Oligonucleotide and Peptide Synthesizer—Pet Oligator. Int. J. Peptide Res. Ther. 13(1-2):367-376 (2007).
Leproust et al.: Synthesis of high-quality libraries of long (150mer) oligonucleotides by a novel depurination controlled process. Nucleic Acids Research. 38(8):2522-2540 (2010).
Lewontin and Harti, Population genetics in forensic DNA typing. Science, 254:1745-1750, 1991.
Ma et al.: DNA synthesis, assembly and application in synthetic biology. Current Opinion in Chemical Biology. 16:260-267 (2012).
Ma et al.: Versatile surface functionalization of cyclic olefin copolymer (COC) with sputtered SiO2 thin film for potential BioMEMS applications. Journal of Materials Chemistry. 11 pages (2009).
Mazor et al.: Isolation of Full-Length IgG Antibodies from Combinatorial Libraries Expressed in *Escherichia coli*; Antony S. Dimitrov (ed.), Therapeutic Antibodies: Methods and Protocols, vol. 525, Chapter 11, pp. 217-239 (2009).

(56) References Cited

OTHER PUBLICATIONS

McBride & Caruthers. An investigation of several deoxynucleoside phosphoramidites useful for synthesizing deoxyoligonucleotides. Tetrahedron Lett. 24:245-248 (1983).
Mitra et al.: In situ localized amplification and contact replication of many individual DNA molecules. Nucleic Acids Res. 27(24):e34 (1999).
Morin et al.: Profiling the HeLa S3 transcriptome using randomly primed cDNA and massively parallel short-read sequencing. Biotechniques. 45:81-94 (2008).
Opposition to European Patent No. 3030682 filed Mar. 3, 2021.
PCT/US2014/049834 International Preliminary Report on Patentability dated Feb. 18, 2016.
PCT/US2014/049834 International Search Report and Written Opinion dated Mar. 19, 2015.
PCT/US2145/049834 Invitation to Pay Additional Fees and, where applicable, protest fee dated Jan. 5, 2015.
Pirrung. How to make a DNA chip. Angew. Chem. Int. Ed. 41:1276-1289 (2002).
Pray. Discovery of DNA Structure and Function: Watson and Crick. Nature Education.6 pages (2008) available at: http://www.nature.com/scitable/topicpage/discovery-of-dna-structure-and-function-watson-397.
Quan et al.: Parallel on-chip gene synthesis and application to optimization of protein expression. Nature Biotechnology. 29:449-452 (2011).
Rafalski and Morgante, Corn and humans: recombination and linkage disequilibrium in two genomes of similar size. Trends in Genetics. 20(2):103-111. (2004).
Rogozin et al.: Origin and evolution of spliceosomal introns. Biology Direct, 7:11 (2012).
Saaem et al.: In situ synthesis of DNA microarray on functionalized cyclic olefin copolymer substrate ACS Applied Materials & Interfaces. 2(2):491-497 (2010).
Sargolzaei et al.: Extent of linkage disequilibrium in Holstein cattle in North America. J.Dairy Science. 91:2106-2117 (2007).
Srivannavit et al.: Design and fabrication of microwell array chips for a solution-based, photogenerated acid-catalyzed parallel oligonucleotide DNA synthesis. Sensors and Actuators A. 116:150-160 (2004).
Steel. The Flow-Thru Chip A Three-dimensional biochip platform. In: Schena, Microarray Biochip Technology, Chapter 5, Natick, MA: Eaton Publishing, 2000, 33 pages.
Taylor et al.: Impact of surface chemistry and blocking strategies on DNA microarrays. Nucleic Acids Research, 31(16):e87 19 pages (2003).
Tian et al.: Accurate multiplex gene synthesis from programmable DNA microchips. Nature. 432(7020):1050-1054 (2004).
U.S. Appl. No. 14/452,429 Notice of Allowance dated Jun. 7, 2016.
U.S. Appl. No. 14/452,429 Office Action dated Apr. 9, 2015.
U.S. Appl. No. 14/452,429 Office Action dated Oct. 21, 2015.
U.S. Appl. No. 14/452,429 Restriction Requirement dated Dec. 12, 2014.
U.S. Appl. No. 14/885,962 Notice of Allowance dated Nov. 8, 2017 and Sep. 29, 2017.
U.S. Appl. No. 14/885,962 Office Action dated Dec. 16, 2016.
U.S. Appl. No. 14/885,962 Office Action dated Sep. 8, 2016.
U.S. Appl. No. 14/885,962 Restriction Requirement dated Mar. 1, 2016.
U.S. Appl. No. 14/885,963 Notice of Allowance dated May 24, 2016.
U.S. Appl. No. 14/885,963 Office Action dated Feb. 5, 2016.
U.S. Appl. No. 14/885,965 Office Action dated Aug. 28, 2018.
U.S. Appl. No. 14/885,965 Office Action dated Aug. 30, 2017.
U.S. Appl. No. 14/885,965 Office Action dated Feb. 10, 2017.
U.S. Appl. No. 14/885,965 Office Action dated Feb. 18, 2016.
U.S. Appl. No. 14/885,965 Office Action dated Jan. 4, 2018.
U.S. Appl. No. 14/885,965 Office Action dated Jul. 7, 2016.
U.S. Appl. No. 15/187,714 Final Office Action dated Sep. 17, 2019.
U.S. Appl. No. 15/187,714 Office Action dated Apr. 4, 2019.
U.S. Appl. No. 15/187,714 Restriction Requirement dated Sep. 17, 2018.
U.S. Appl. No. 15/187,721 Notice of Allowance dated Dec. 7, 2016.
U.S. Appl. No. 15/187,721 Office Action dated Oct. 14, 2016.
U.S. Appl. No. 15/233,835 Notice of Allowance dated Oct. 4, 2017.
U.S. Appl. No. 15/233,835 Office Action dated Feb. 8, 2017.
U.S. Appl. No. 15/233,835 Office Action dated Jul. 26, 2017.
U.S. Appl. No. 15/233,835 Restriction Requirement dated Nov. 4, 2016.
U.S. Appl. No. 15/245,054 Notice of Allowance dated Dec. 14, 2017.
U.S. Appl. No. 15/245,054 Office Action dated Mar. 21, 2017.
U.S. Appl. No. 15/245,054 Office Action dated Oct. 19, 2016.
U.S. Appl. No. 15/377,547 Final Office Action dated Feb. 8, 2019.
U.S. Appl. No. 15/377,547 Office Action dated Jul. 27, 2018.
U.S. Appl. No. 15/377,547 Office Action dated Mar. 24, 2017.
U.S. Appl. No. 15/377,547 Office Action dated Nov. 30, 2017.
U.S. Appl. No. 15/602,991 Final Office Action dated Dec. 13, 2018.
U.S. Appl. No. 15/602,991 Notice of Allowance dated Oct. 25, 2017.
U.S. Appl. No. 15/602,991 Office Action dated May 31, 2018.
U.S. Appl. No. 15/602,991 Office Action dated May 31, 2019.
U.S. Appl. No. 15/602,991 Office Action dated Sep. 21, 2017.
U.S. Appl. No. 15/603,013 Final Office Action dated Nov. 6, 2019.
U.S. Appl. No. 15/603,013 Office Action dated Jan. 30, 2018.
U.S. Appl. No. 15/603,013 Office Action dated Jul. 10, 2018.
U.S. Appl. No. 15/603,013 Office Action dated Jun. 26, 2019.
U.S. Appl. No. 15/603,013 Office Action dated Oct. 20, 2017.
U.S. Appl. No. 15/729,564 Final Office Action dated Dec. 13, 2018.
U.S. Appl. No. 15/729,564 Office Action dated Jan. 8, 2018.
U.S. Appl. No. 15/729,564 Office Action dated Jun. 6, 2018.
U.S. Appl. No. 15/729,564 Office Action dated May 30, 2019.
U.S. Appl. No. 15/991,992 Office Action dated May 21, 2020.
U.S. Appl. No. 15/991,992 Restriction Requirement dated Mar. 10, 2020.
U.S. Appl. No. 16/039,256 Final Office Action dated Mar. 30, 2021.
U.S. Appl. No. 16/039,256 Office Action dated Aug. 20, 2020.
U.S. Appl. No. 16/039,256 Restriction Requirement dated May 18, 2020.
U.S. Appl. No. 16/409,608 Office Action dated Sep. 9, 2019.
U.S. Appl. No. 16/535,777 Final Office Action dated Oct. 20, 2020.
U.S. Appl. No. 16/535,777 Office Action dated Feb. 8, 2021.
U.S. Appl. No. 16/535,777 Office Action dated Jan. 23, 2020.
U.S. Appl. No. 16/535,779 First Action Interview dated Feb. 10, 2020.
Van Tassell et al.: SNP discovery and allele frequency estimation by deep sequencing of reduced representation libraries. Nature Methods. 5:247-252 (2008).
Xu et al.: Design of 240,000 orthogonal 25mer DNA barcode probes. PNAS. 106(7):2289-2294 (2009).
Hasin-Brumshtein et al.: The Effects of Mismatches on DNA Capture by Hybridization. Twist WhitePaper. 6 pages (May 7, 2019).
Kent et al.: Polymerase theta is a robust terminal transferase that oscillates between three different mechanisms during end-joining. Elife. 5:1-25 (2016).
PCT/US2021/055454 International Search Report and Written Opinion dated Feb. 16, 2022.
U.S. Appl. No. 16/039,256 Office Action dated May 10, 2022.
U.S. Appl. No. 16/737,401 Final Office Action dated Jun. 13, 2022.

METHODS OF SYNTHESIZING OLIGONUCLEOTIDES USING TETHERED NUCLEOTIDES

CROSS-REFERENCE

This application claims the benefit of U.S. Provisional Application No. 63/093,716, filed Oct. 19, 2020, which applications is incorporated herein by reference.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF SUMMARY

Provided herein are compositions comprising a complex according to the following formula:

$$A\text{-}L\text{-}B \quad \text{(Formula I)}$$

wherein: A comprises a polymerase; B comprises a nucleotide; and L comprises a chemical linker that covalently links the polymerase to a terminal phosphate group of the nucleotide, wherein the polymerase is configured to catalyze covalent addition of the nucleotide onto a 3' hydroxyl of a polynucleotide, and subsequent extension of the polynucleotide. Further provided herein are compositions, wherein the polymerase is a template-independent polymerase. Further provided herein are compositions, wherein the polymerase is terminal deoxynucleotidyl transferase (TdT). Further provided herein are compositions, wherein the polymerase is polymerase theta. Further provided herein are compositions, wherein the polymerase theta is encoded by POLQ. Further provided herein are compositions, wherein the chemical linker is an acid-labile linker. Further provided herein are compositions, wherein the chemical linker is a base-labile linker. Further provided herein are compositions, wherein the chemical linker is cleaved using irradiation. Further provided herein are compositions, wherein the chemical linker is cleaved using an enzyme. Further provided herein are compositions, wherein the enzyme is a peptidase. Further provided herein are compositions, wherein the enzyme is an esterase. Further provided herein are compositions, wherein the chemical linker is a pH-sensitive linker. Further provided herein are compositions, wherein the chemical linker is an amine-to-thiol crosslinker. Further provided herein are compositions, wherein the chemical linker is a thiomaleamic acid linker. Further provided herein are compositions, wherein the chemical linker is a photo-cleavable linker. Further provided herein are compositions, wherein the photo-cleavable linker is selected from the group consisting of orthonitrobenzyl-based linker, phenacyl linker, alkoxybenzoin linker, chromium arene complex linker, NpSSMpact linker, pivaloylglycol linker, and any combination thereof. Further provided herein are compositions, wherein the chemical linker is selected from the group consisting of a silyl linker, an alkyl linker, a polyether linker, a polysulfonyl linker, a polysulfoxide linker, and any combination thereof. Further provided herein are compositions, wherein the nucleotide comprises at least 3 phosphate groups. Further provided herein are compositions, wherein the nucleotide is selected from the group consisting of nucleoside triphosphate, nucleoside tetraphosphate, nucleoside pentaphosphate, nucleoside hexaphosphate, nucleoside heptaphosphate, nucleoside octaphosphate, nucleoside nonaphosphate, and any combination thereof. Further provided herein are compositions, wherein the nucleotide is selected from the group consisting of deoxyadenosine triphosphate (dATP), deoxyguanosine triphosphate (dGTP), deoxycytidine triphosphate (dCTP), deoxythymidine triphosphate (dTTP), deoxyadenosine tetraphosphate, deoxyguanosine tetraphosphate, deoxycytidine tetraphosphate, deoxythymidine tetraphosphate, deoxyadenosine pentaphosphate, deoxyguanosine pentaphosphate, deoxycytidine pentaphosphate, deoxythymidine pentaphosphate, deoxyadenosine hexaphosphate, deoxyguanosine hexaphosphate, deoxycytidine hexaphosphate, deoxythymidine hexaphosphate, and any combination thereof. Further provided herein are compositions further comprising a reversible terminator. Further provided herein are compositions, wherein the reversible terminator is configured to terminate extension of the polynucleotide. Further provided herein are compositions, wherein the reversible terminator is a 3' O-modified or base-modified reversible terminator. Further provided herein are compositions, wherein the reversible terminator comprises an allyl, hydroxylamine, acetate, benzoate, phosphate, azidomethyl, or amide group.

Provided herein are methods of synthesizing a polynucleotide, comprising: a) contacting a polynucleotide with a complex according to the following formula:

$$A\text{-}L\text{-}B \quad \text{(Formula I)}$$

wherein: A comprises a polymerase; B comprises a nucleotide; and L comprises a chemical linker that covalently links the polymerase to a terminal phosphate group of the nucleotide, wherein the polymerase is configured to catalyze covalent addition of the nucleotide onto a 3' hydroxyl of a polynucleotide, and subsequent extension of the polynucleotide; and b) cleaving the polymerase from the polynucleotide, wherein the cleaving does not leave a part of the linker on the polynucleotide. Further provided herein are methods, wherein steps a)-b) are repeated to produce an extended polynucleotide. Further provided herein are methods, wherein the extended polynucleotide has a defined sequence. Further provided herein are methods, wherein the extended polynucleotide comprises at least about 50 nucleotides. Further provided herein are methods, wherein the extended polynucleotide comprises at least about 100 nucleotides. Further provided herein are methods, wherein the extended polynucleotide comprises at least about 200 nucleotides. Further provided herein are methods, wherein the polymerase is a template-independent polymerase. Further provided herein are methods, wherein the polymerase is terminal deoxynucleotidyl transferase (TdT). Further provided herein are methods, wherein the polymerase is polymerase theta. Further provided herein are methods, wherein the polymerase theta is encoded by POLQ. Further provided herein are methods, wherein the chemical linker is an acid-labile linker. Further provided herein are methods, wherein the chemical linker is a base-labile linker. Further provided herein are methods, wherein the chemical linker is cleaved using irradiation. Further provided herein are methods, wherein the chemical linker is cleaved using an enzyme. Further provided herein are methods, wherein the enzyme is a peptidase. Further provided herein are methods, wherein the enzyme is an esterase. Further provided herein are methods, wherein the chemical linker is a pH-sensitive linker. Further provided herein are methods, wherein the chemical linker is an amine-to-thiol crosslinker. Further provided herein are methods, wherein the chemical linker is a thiomaleamic acid linker. Further provided herein are methods, wherein the chemical linker is a photo-cleavable linker. Further provided herein are methods, wherein the photo-cleavable linker is selected from the group consisting of orthonitrobenzyl-based linker, phenacyl linker, alkoxybenzoin linker, chromium arene complex linker, NpSSMpact linker, pivaloylglycol linker, and any combination thereof. Further provided herein are methods, wherein the chemical linker is selected from the group consisting of a silyl linker, an alkyl linker, a polyether linker, a polysulfonyl linker, a polysulfoxide linker, and any combination thereof. Further provided herein are methods, wherein the nucleotide comprises at least 3 phosphate groups. Further provided herein are methods, wherein the nucleotide is selected from the group consisting of nucleoside triphosphate, nucleoside tetraphosphate, nucleoside pentaphosphate, nucleoside hexaphosphate, nucleoside heptaphosphate, nucleoside octaphosphate, nucleoside nonaphosphate and any combination thereof. Further provided herein are methods, wherein the nucleotide is selected from the group consisting of deoxyadenosine triphosphate (dATP), deoxyguanosine triphosphate (dGTP), deoxycytidine triphosphate (dCTP), deoxythymidine triphosphate (dTTP), deoxyadenosine tetraphosphate, deoxyguanosine tetraphosphate, deoxycytidine tetraphosphate, deoxythymidine tetraphosphate, deoxyadenosine pentaphosphate, deoxyguanosine pentaphosphate, deoxycytidine pentaphosphate, deoxythymidine pentaphosphate, deoxyadenosine hexaphosphate, deoxyguanosine hexaphosphate, deoxycytidine hexaphosphate, deoxythymidine hexaphosphate, and any combination thereof. Further provided herein are methods further comprising following step b) contacting the polynucleotide with a reversible terminator. Further provided herein are methods, wherein the reversible terminator is a 3' O-modified or base-modified reversible terminator. Further provided herein are methods, wherein the reversible terminator comprises comprise an allyl, hydroxylamine, acetate, benzoate, phosphate, azidomethyl, or amide group. Further provided herein are methods, wherein the polynucleotide is extended by at least about 10 nucleotides per hour. Further provided herein are methods, wherein the method comprises a coupling efficiency of at least about 95%. Further provided herein are methods, wherein the method comprises a total average error rate of less than about 1:1000.

DETAILED DESCRIPTION

Definitions

Figure 1:
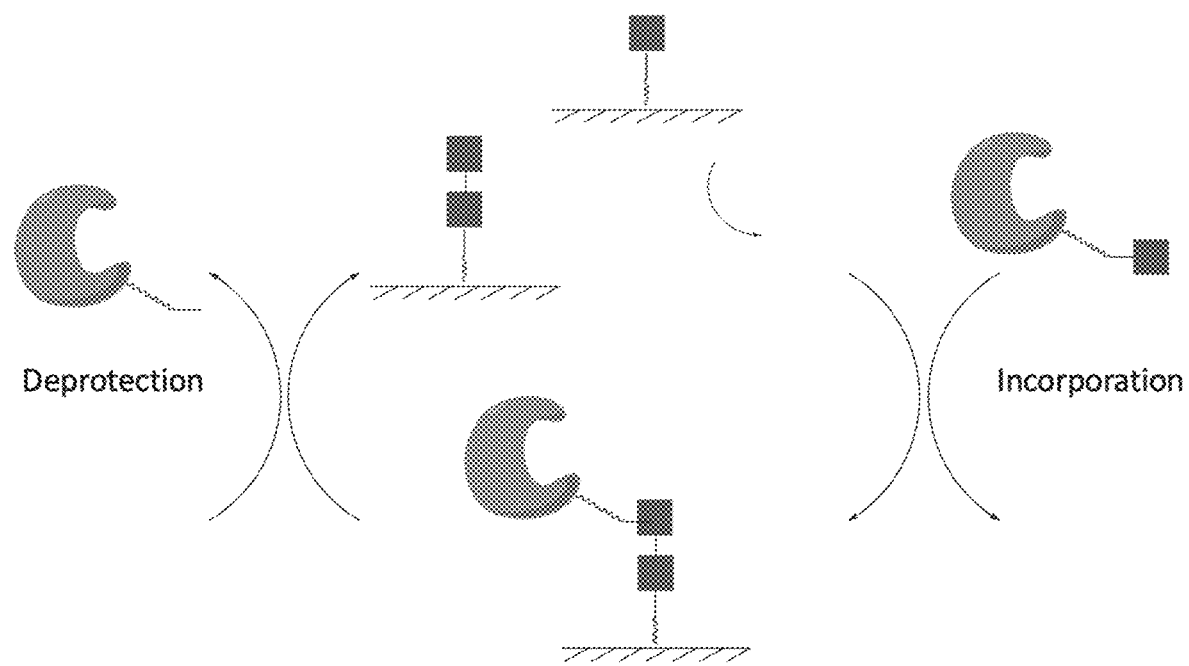
FIG. 1 illustrates a general enzymatic polynucleotide synthesis using terminal deoxynucleotidyl transferase (TdT).
Figure 2:
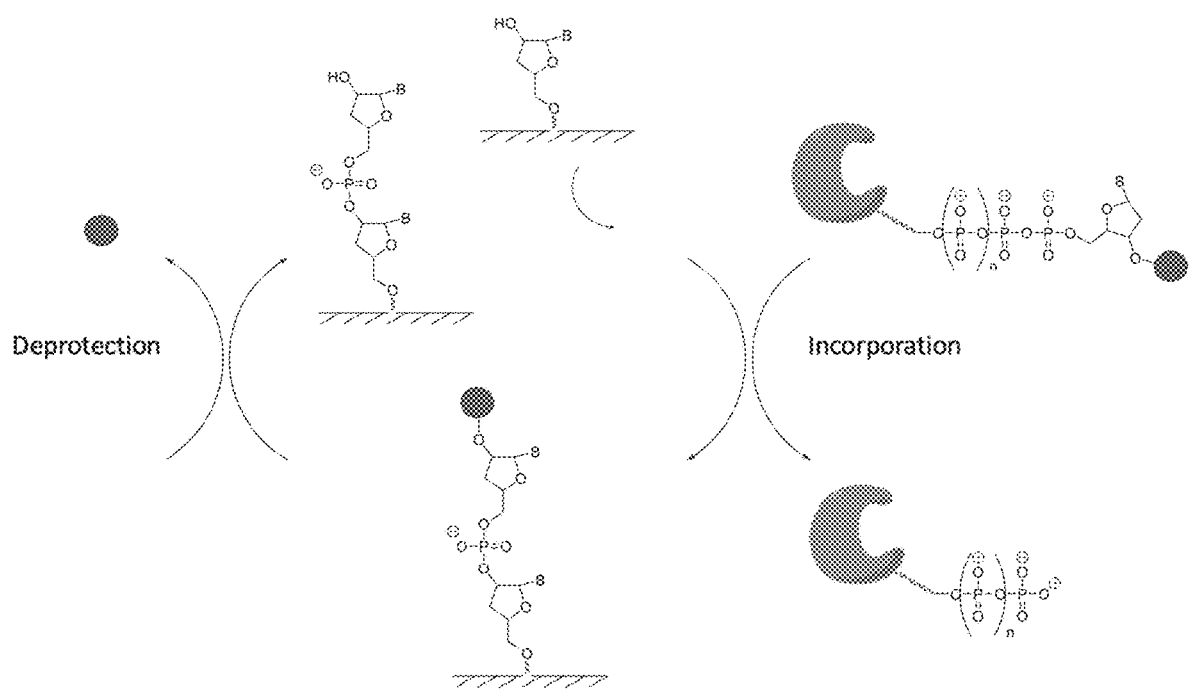
FIG. 2 illustrates enzymatic polynucleotide synthesis using TdT conjugated to a terminal phosphate group.

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the disclosure, subject to any specifically excluded limit in the stated range. Where the stated range includes one or both of the limits, ranges excluding either or both of those included limits are also included in the disclosure, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers+/−10% thereof, or 10% below the lower listed limit and 10% above the higher listed limit for the values listed for a range.

Unless specifically stated, as used herein, the term "nucleic acid" encompasses double- or triple-stranded nucleic acids, as well as single-stranded molecules. In double- or triple-stranded nucleic acids, the nucleic acid strands need not be coextensive (i.e., a double-stranded nucleic acid need not be double-stranded along the entire length of both strands). Nucleic acid sequences, when provided, are listed in the 5' to 3' direction, unless stated otherwise. Methods described herein provide for the generation of isolated nucleic acids. Methods described herein additionally provide for the generation of isolated and purified nucleic acids. A "nucleic acid" as referred to herein can comprise at least 5, 10, 20, 30, 40, 50, 60, 70, 80, 90, 100, 125, 150, 175, 200, 225, 250, 275, 300, 325, 350, 375, 400, 425, 450, 475, 500, 600, 700, 800, 900, 1000, 1100, 1200, 1300, 1400, 1500, 1600, 1700, 1800, 1900, 2000, or more bases in length. Moreover, provided herein are methods for the synthesis of any number of polypeptide-segments encoding nucleotide sequences, including sequences encoding non-ribosomal peptides (NRPs), sequences encoding non-ribosomal peptide-synthetase (NRPS) modules and synthetic variants, polypeptide segments of other modular proteins, such as antibodies, polypeptide segments from other protein families, including non-coding DNA or RNA, such as regulatory sequences e.g. promoters, transcription factors, enhancers, siRNA, shRNA, RNAi, miRNA, small nucleolar RNA derived from microRNA, or any functional or structural DNA or RNA unit of interest. The following are non-limiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, complementary DNA (cDNA), which is a DNA representation of mRNA, usually obtained by reverse transcription of messenger RNA (mRNA) or by amplification; DNA molecules produced synthetically or by amplification, genomic DNA, recombinant polynucleotides, branched polynucleotides, plasmids, vectors, isolated DNA of any sequence, isolated RNA of any sequence, nucleic acid probes, and primers. cDNA encoding for a gene or gene fragment referred herein may comprise at least one region encoding for exon sequences without an intervening intron sequence in the genomic equivalent sequence. cDNA described herein may be generated by de novo synthesis.

Provided herein are methods and compositions for production of polynucleotides. Polynucleotides may also be referred to as oligonucleotides or oligos.

Polynucleotide Synthesis

Terminal deoxynucleotidyl transferase (TdT) is a polymerase that adds deoxynucleotide triphosphates (dNTPs) to the 3' end of single-stranded DNA. Disclosed herein are methods of enzymatically synthesizing polynucleotides using TdT. FIG. 1 illustrates a general two-step enzymatic polynucleotide synthesis cycle using TdT. A two-step method is used to extend polynucleotides using TdT-dNTP conjugates consisting of a TdT molecule site-specifically labeled with a dNTP via a cleavable linker. The synthetic cycle comprises two steps: 1) In the extension step, a DNA primer is exposed to an excess of TdT-dNTP conjugate. Once the tethered nucleotide is incorporated into the 3' end of the primer, the conjugate becomes covalently attached, which prevents extensions by other TdT-dNTP molecules. Each TdT molecule is conjugated to a single dNTP molecule that is incorporated into a primer. 2) In the deprotection step, the excess TdT-dNTP conjugates are inactivated, and the linkage between the incorporated nucleotide and TdT is cleaved. Cleavage of TdT releases the primer for further extension. The two-step process can be repeated to generate a defined sequence.

Described herein are methods of synthesizing polynucleotides comprising using a complex according to the following formula:

$$A\text{-}L\text{-}B \qquad \text{(Formula I)}$$

wherein A comprises a polymerase; B comprises a nucleotide; and L comprises a chemical linker that covalently links the polymerase to a terminal phosphate group of the nucleotide, wherein the polymerase is configured to catalyze covalent addition of the nucleotide onto a 3' hydroxyl of a polynucleotide, and subsequent extension of the polynucleotide.

In some embodiments, the polymerase is site-specifically conjugated to a terminal phosphate group of a phosphorylated nucleoside to form a tethered molecule. A phosphorylated nucleoside, in some embodiments, is referred to as a nucleotide. When a polymerase incorporates the tethered phosphorylated nucleoside into a primer, the polymerase can remain covalently attached to a terminal phosphate group of the 3' end of the primer via a linker, blocking further elongation by other polymerase conjugates. The linker can then be cleaved to deprotect the 3' end of the primer for subsequent extension. The process can be repeated to elongate the polynucleotide to a desired length and sequence.

In some embodiments, the phosphorylated nucleoside (e.g., nucleotide) to be tethered to the polymerase is a nucleoside comprising at least one phosphate group. In some embodiments, the nucleoside comprises at least 1, 2, 3, 4, 5, 6, 7, 8, 9, or more than 9 phosphate groups. In some embodiments, the nucleoside comprises at least 3 phosphate groups. In some embodiments, the phosphorylated nucleoside is adenosine, cytidine, uridine, or guanosine, each of which comprises at least one phosphate group. In some embodiments, the phosphorylated nucleoside is a deoxynucleoside comprising at least one phosphate group. In some embodiments, the phosphorylated nucleoside is a deoxynucleoside comprising at least 3 phosphate groups. In some embodiments, the deoxynucleoside comprises at least 1, 2, 3, 4, 5, 6, 7, 8, 9, or more than 9 phosphate groups. In some embodiments, the phosphorylated nucleoside is deoxyadenosine, deoxycytidine, deoxythymidine, or deoxyguanosine, each of which comprises at least one phosphate group. In some embodiments, the phosphorylated nucleoside is a nucleoside triphosphate, such as dNTP. In some embodiments, the phosphorylated nucleoside is a nucleoside tetraphosphate, nucleoside pentaphosphate, a nucleoside hexaphosphate, a nucleoside heptaphosphate, nucleoside octaphosphate, or a nucleoside nonaphosphate. In some embodiments, the phosphorylated nucleoside is a nucleoside hexaphosphate. In some embodiments, the phosphorylated nucleoside is a nucleoside triphosphate. In some embodiments, the phosphorylated nucleoside is selected from the group consisting of deoxyadenosine triphosphate (dATP), deoxyguanosine triphosphate (dGTP), deoxycytidine triphosphate (dCTP), deoxythymidine triphosphate (dTTP), deoxyadenosine tetraphosphate, deoxyguanosine tetraphosphate, deoxycytidine tetraphosphate, deoxythymidine tetraphosphate, deoxyadenosine pentaphosphate, deoxyguanosine pentaphosphate, deoxycytidine pentaphosphate, deoxythymidine pentaphosphate, deoxyadenosine hexaphosphate, deoxyguanosine hexaphosphate, deoxycytidine hexaphosphate, deoxythymidine hexaphosphate, and any combination thereof.

The methods described herein can use enzymatically synthesized polynucleotides using a solid support. In some embodiments, the methods of the disclosure can synthesize polynucleotides in the wells of a multi-well plate, for example, 96-well or 384-well plates. In some embodiments, the methods of the disclosure can synthesize polynucleotides using a non-swellable or low-swellable solid support. In some embodiments, the methods of the disclosure can synthesize polynucleotides using controlled pore glass (CPG) or microporous polystyrene (MPPS). In some embodiments, the methods of the disclosure can synthesize polynucleotides on CPG treated with a surface-coating material. In some embodiments, the methods of the disclosure can synthesize polynucleotides on CPG treated with (3-aminopropyl)triethoxysilane (3-aminopropyl CPG). In some embodiments, the methods of the disclosure can synthesize polynucleotides on long chain aminoalkyl (LCAA) CPG. In some embodiments, the methods of the disclosure can synthesize polynucleotides using CPG with average pore sizes of about 500, about 1000, about 1500, about 2000, or about 3000 Å.

Provided herein are various surfaces for enzymatically synthesized polynucleotides. In some embodiments, the surface comprises one or more reverse phosphoramidites. In some embodiments, the surface comprises a linker attached on the surface. In some embodiments, the linker is attached on the surface after treatment with diethylamine. In some embodiments, the surface comprises dT.

In some embodiments, the surface comprises at least one hydrophilic polymer. The hydrophilic polymer comprises, in various embodiments, polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(-hydroxylethyl methacrylate) (PHEMA), poly(oligo(ethylene glycol) methyl ether methacrylate) (POEGMA), polyglutamic acid (PGA), poly-lysine, polyglucoside, streptavidin, and dextran. In some embodiments, the surface comprises polyethylene glycol (PEG).

In some embodiments, the surface comprises a siloxane monomer or polymer. In some embodiments, the siloxane monomer or polymer comprises an epoxide functional group. In some embodiments, the siloxane monomer or polymer thereof comprises one or more monomers selected from (3-glycidylpropyl)trimethoxysilane (GPTMS), Diethoxy(3-glycidyloxypropyl)methylsilane, 3-Glycidoxypropyldimethoxymethylsilane, 2-(3,4-epoxycyclohexyl)ethyltriethoxysilane, 2-(3,4-epoxycyclohexyl)ethyltrimethoxysilane, or combinations thereof. In some embodiments, the siloxane monomer is GPTMS. In some embodiments, the siloxane monomer is Diethoxy(3-glycidyloxypropyl)methylsilane. In some embodiments, the siloxane monomer is 3-Glycidoxypropyldimethoxymethylsilane. In some embodiments, the siloxane monomer is 2-(3,4-epoxycyclohexyl)ethyltriethoxysilane. In some embodiments, the siloxane monomer is 2-(3,4-epoxycyclohexyl)ethyltrimethoxysilane.

In some embodiments, the surfaces comprise heptadecafluorodecyltrichlorosilane, poly(tetrafluoroethylene), octadecyltrichlorosilane, methyltrimethoxysilane, nonafluorohexyltrimethoxysilane, vinyltriethoxysilane, paraffin wax, ethyltrimethoxysilane, propyltrimethoxysilane, glass, poly(chlorotrifluoroethylene), polypropylene, poly(propylene oxide), polyethylene, trifluoropropyltrimethoxysilane, 3-(2-aminoethyl)aminopropyltrimethoxysilane, polystyrene, p-tolyltrimethoxysilane, cyanoethyltrimethoxysilane, aminopropyltriethoxysilane, acetoxypropyltrimethoxysilane, poly(methyl methacrylate), poly(vinyl chloride), phenyltrimethoxysilane, chloropropyltrimethoxysilane, mercaptopropyltrimethoxysilane, glycidoxypropyltrimethoxysilane, poly(ethylene terephthalate), copper (dry), poly(ethylene oxide), aluminum, nylon 6/6, iron (dry), glass, sodalime (dry), titanium oxide (anatase), ferric oxide, tin oxide, or combinations thereof.

Provided herein are various support for enzymatically synthesized polynucleotides. In some embodiments, the polynucleotides described herein are synthesized on one or more solid supports. Exemplary solid supports include, for example, slides, beads, chips, particles, strands, gels, sheets, tubing, spheres, containers, capillaries, pads, slices, films, plates, polymers, or a microfluidic device. Further, the solid supports may be biological, nonbiological, organic, inorganic, or combinations thereof. On supports that are substantially planar, the support may be physically separated into regions, for example, with trenches, grooves, wells, or chemical barriers (e.g., hydrophobic coatings, etc.). Supports may also comprise physically separated regions built into a surface, optionally spanning the entire width of the surface. Suitable supports for improved oligonucleotide synthesis are further described herein. In some embodiments, the polynucleotides are provided on a solid support for use in a microfluidic device, for example, as part of the PCA reaction chamber. In some embodiments, the polynucleotides are synthesized and subsequently introduced into a microfluidic device.

Provided herein are devices for enzymatically synthesized polynucleotides comprising layers of materials. Such devices may comprise any number of layers of materials comprising conductors, semiconductors, or insulative materials. Various layers of such devices are in some instances combined to form addressable solid supports. Layers or surfaces of such devices may be in fluid communication with solvents, solutes, or other reagents used during polynucleotide synthesis. Further described herein are devices comprising a plurality of surfaces. In some instances, surfaces comprise features for polynucleotides synthesis in proximity to conducting materials. In some instances, devices described herein comprise 1, 2, 5, 10, 50, 100, or even thousands of surfaces per device. In some instances, a voltage is applied to one or more layers of a device described herein to facilitate polynucleotide synthesis. In some instances, a voltage is applied to one or more layers of a device described herein to facilitate a step in polynucleotide synthesis, such as deblocking. Different layers on different surfaces of different devices are often energized with a voltage at varying times or with varying voltages. For example, a positive voltage is applied to a first layer, and a negative voltage is applied to a second layer of the same or a different device. In some instances, one or more layers on different devices are energized, while others are disconnected from a ground. In some instances, base layers comprise additional circuitry, such as complementary metal-oxide-semiconductors (CMOS) devices. In some instances, various layers of one or more devices are connected laterally via routing, and/or vertically with vias. In some instances, various layers of one or more devices are connected laterally via routing, and/or vertically with vias to a CMOS layer. In some instances, various layers of one or more devices are connected to a CMOS device via wire bonds, pogo pin contacts, or through Si Vias (TSV).

The substrates, the solid support, or the devices described herein may be fabricated from a variety of materials, suitable for the methods and compositions of the disclosure described herein. In certain embodiments, the materials from which the substrates/solid supports of the comprising the disclosure are fabricated exhibit a low level of oligonucleotide binding. In some situations, material that are transparent to visible and/or UV light can be employed. Materials that are sufficiently conductive, e.g. those that can form uniform electric fields across all or a portion of the substrates/solids support described herein, can be utilized. In some embodiments, such materials may be connected to an electric ground. In some cases, the substrate or solid support can be heat conductive or insulated. The materials can be chemical resistant and heat resistant to support chemical or biochemical reactions such as a series of oligonucleotide synthesis reaction. For flexible materials, materials of interest can include: nylon, both modified and unmodified, nitrocellulose, polypropylene, and the like. For rigid materials, specific materials of interest include: glass; fuse silica; silicon, plastics (for example polytetraflouroethylene, polypropylene, polystyrene, polycarbonate, and blends thereof, and the like); metals (for example, gold, platinum, and the like). The substrate, solid support or reactors can be fabricated from a material selected from the group consisting of silicon, polystyrene, agarose, dextran, cellulosic polymers, polyacrylamides, polydimethylsiloxane (PDMS), and glass.

In various embodiments, surface modifications are employed for the chemical and/or physical alteration of a surface by an additive or subtractive process to change one or more chemical and/or physical properties of a substrate surface or a selected site or region of a substrate surface. For example, surface modification may involve (1) changing the wetting properties of a surface, (2) functionalizing a surface, i.e., providing, modifying or substituting surface functional groups, (3) defunctionalizing a surface, i.e., removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface.

Described herein are methods for enzymatically synthesizing polynucleotides, wherein the methods comprise using a chain-elongating enzyme. In some instances, the chain-elongating enzyme is a polymerase. In some instances, the polymerase is a template-independent polymerase. In some instances, the polymerase is a RNA polymerase or DNA polymerase. In some instances, the polymerase is a DNA polymerase. Examples of DNA polymerases include polA, polB, polC, polD, polY, polX, reverse transcriptases (RT), and high-fidelity polymerases. In some instances, the polymerase is a modified polymerase.

In some embodiments, the polymerase comprises Φ29, B103, GA-1, PZA, Φ15, BS32, M2Y, Nf, G1, Cp-1, PRD1, PZE, SFS, Cp-5, Cp-7, PR4, PRS, PR722, L17, ThermoSequenase®, 9° Nm™, Terminator™ DNA polymerase, Tne, Tma, Tfl, Tth, Tli, Stoffel fragment, Vent™ and Deep Vent™ DNA polymerase, KOD DNA polymerase, Tgo, JDF-3, Pfu, Taq, T7 DNA polymerase, T7 RNA polymerase, PGB-D, UlTma DNA polymerase, E. coli DNA polymerase I, E. coli DNA polymerase III, archaeal DP1I/DP2 DNA polymerase II, 9° N DNA Polymerase, Taq DNA polymerase, Phusion® DNA polymerase, Pfu DNA polymerase, SP6 RNA polymerase, RB69 DNA polymerase, Avian Myeloblastosis Virus (AMV) reverse transcriptase, Moloney Murine Leukemia Virus (MMLV) reverse transcriptase, SuperScript® II reverse transcriptase, and SuperScript® III reverse transcriptase.

In some embodiments, the polymerase is DNA polymerase 1-Klenow fragment, Vent polymerase, Phusion® DNA polymerase, KOD DNA polymerase, Taq polymerase, T7 DNA polymerase, T7 RNA polymerase, Terminator™ DNA polymerase, POLB polymerase, SP6 RNA polymerase, E. coli DNA polymerase I, E. coli DNA polymerase III, Avian Myeloblastosis Virus (AMV) reverse transcriptase, Moloney Murine Leukemia Virus (MMLV) reverse transcriptase, SuperScript® II reverse transcriptase, or SuperScript® III reverse transcriptase.

The polymerase molecules used in the methods described herein can be polymerase theta, a DNA polymerase, or any enzyme that can extend nucleotide chains. In some embodiments, the polymerase is tri29. In some embodiments, the polymerase is a protein with pockets that work around terminal phosphate groups, for example, a triphosphate group.

In some embodiments, the described methods use TdT with 1, 2, 3, 4, 5, 6, 7, 8, 9, or 10 amino acid mutations to synthesize defined polynucleotides. In some embodiments, the described method uses TdT with 1, 2, 3, 4, 5, 6, 7, 8, 9, or 10 amino acid mutations to a surface-accessible amino acid residue. In some embodiments, the TdT is a variant of TdT. In some embodiments, the variant of TdT comprises a cysteine mutation (e.g., NTT-1). In some embodiments, the variant of TdT is NTT-1, NTT-2, or NTT-3. In some instances, the variant TdT comprises at least 70%, 80%, 90%, or 95% sequence identity to wild-type TdT.

In some embodiments, the described methods use polymerase theta with 1, 2, 3, 4, 5, 6, 7, 8, 9, or 10 amino acid mutations to synthesize defined polynucleotides. In some embodiments, the described method uses polymerase theta with 1, 2, 3, 4, 5, 6, 7, 8, 9, or 10 amino acid mutations to a surface-accessible amino acid residue. In some embodiments, the polymerase theta is a variant of polymerase theta. In some instances, the variant polymerase theta comprises at least 70%, 80%, 90%, or 95% sequence identity to wild-type polymerase theta. In some embodiments, the polymerase theta is encoded by POLQ.

Enzymes described herein (e.g., TdT), in some embodiments, comprise one or more unnatural amino acids. In some instances, the unnatural amino acid comprises: a lysine analogue; an aromatic side chain; an azido group; an alkyne group; or an aldehyde or ketone group. In some instances, the unnatural amino acid does not comprise an aromatic side chain. In some embodiments, the unnatural amino acid is selected from N6-azidoethoxy-carbonyl-L-lysine (AzK), N6-propargylethoxy-carbonyl-L-lysine (PraK), N6-(propargyloxy)-carbonyl-L-lysine (PrK), p-azido-phenylalanine (pAzF), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (pAMF), p-iodo-L-phenylalanine, m-acetylphenylalanine, 2-amino-8-oxononanoic acid, p-propargyloxyphenylalanine, p-propargyl-phenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, isopropyl-L-phenylalanine, O-allyltyrosine, O-methyl-L-tyrosine, O-4-allyl-L-tyrosine, 4-propyl-L-tyrosine, phosphonotyrosine, tri-O-acetyl-GlcNAcp-serine, L-phosphoserine, phosphonoserine, L-3-(2-naphthyl)alanine, 2-amino-3-((2-((3-(benzyloxy)-3-oxopropyl)amino) ethyl)selanyl)propanoic acid, 2-amino-3-(phenylselanyl) propanoic, selenocysteine, N6-(((2-azidobenzyl)oxy) carbonyl)-L-lysine, N6-(((3-azidobenzyl)oxy)carbonyl)-L-lysine, and N6-(((4-azidobenzyl)oxy)carbonyl)-L-lysine.

In some embodiments, the enzymes described herein are fused to one or more other enzymes. For example, TdT is fused to other enzymes such as helicase.

Various linkers are provided herein for conjugating an enzyme or other nucleic acid (e.g., polymerase) binding moiety to one or more base-pairing moieties, e.g., a modified nucleotide during enzymatic synthesis of the polynucleotides. Conjugation of nucleotides or other base-pairing moieties to linkers may be achieved by any means known in the art of chemical conjugation methods. For example, nucleotides containing base modifications that add a free amine group are contemplated for use in conjugation to linkers as described herein. Primary amines, for example, may be linked to the base in such a manner that they can be reacted with heterobifunctional polyethylene glycol (PEG) linkers to create a nucleotide containing a variable length PEG linker that will still bind properly to the enzyme active site. Examples of such amine-containing nucleotides include 5-propargylamino-dNTPs, 5-propargylamino-NTPs, amino allyl-dNTPs, and amino allyl-NTPs.

In some embodiments, amine-containing nucleotides are suitable for conjugation with PEG-based linkers. PEG linkers may vary in length, for example, from 1-1000, from 1-500, from 1-11, from 1-100, from 1-50, or from 1-10 subunits. In some embodiments, a PEG linker comprises less than 100 subunits. In some embodiments, a PEG linker comprises more than 100 subunits. In some embodiments, a PEG linker comprises more than 500 subunits. In some embodiments, a PEG linker comprises more than 1000 subunits. In some instances, a suitable PEG linker (or a branch thereof) may comprise at least 10 subunits, at least 20 subunits, at least 30 subunits, at least 40 subunits, at least 50 subunits, at least 60 subunits, at least 70 subunits, at least 80 subunits, at least 90 subunits, at least 100 subunits, at least 200 subunits, at least 300 subunits, at least 400 subunits, at least 500 subunits, at least 600 subunits, at least 700 subunits, at least 800 subunits, at least 900 subunits, or at least 1,000 subunits. In some instances, the PEG linker (or a branch thereof) comprises at most 1,000 subunits, at most 900 subunits, at most 800 subunits, at most 700 subunits, at most 600 subunits, at most 500 subunits, at most 400 subunits, at most 300 subunits, at most 200 subunits, at most 100 subunits, at most 90 subunits, at most 80 subunits, at most 70 subunits, at most 60 subunits, at most 50 subunits, at most 40 subunits, at most 30 subunits, at most 30 subunits, or at most 10 subunits. Any of the lower and upper values described in this paragraph may be combined to form a range included within the present disclosure, for example, in some instances a suitable PEG linker (or a branch thereof) may comprise from about 90 subunits to about 400 subunits.

In some embodiments, the linker (e.g., PEG linker) has an apparent average molecular weight, as measured by mass spectrometry, by electrophoretic methods, by size exclusion chromatography, by reverse-phase chromatography, or by any other means as known in the art for the estimation or measurement of the molecular weight of a polymer. In some instances, the apparent average molecular weight of the linker selected for conjugation may be less than about 1,000 Da, less than about 2,000 Da, less than about 3,000 Da, less than about 4,000 Da, less than about 5,000 Da, less than about 7,500 Da, less than about 10,000 Da, less than about 15,000 Da, less than about 20,000 Da, less than about 50,000 Da, less than about 100,000 Da, or less than about 200,000 Da. In some instances, the apparent average molecular weight of the linker selected for conjugation may be more than about 1,000 Da, more than about 2,000 Da, more than about 3,000 Da, more than about 4,000 Da, more than about 5,000 Da, more than about 7,500 Da, more than about 10,000 Da, more than about 15,000 Da, more than about 20,000 Da, more than about 50,000 Da, more than about 100,000 Da, or more than about 200,000 Da.

Examples of other suitable linkers may include, but are not limited to, poly-T and poly-A oligonucleotide strands (e.g., ranging from about 1 base to about 1,000 bases in length), peptide linkers (e.g., poly-glycine or poly-alanine ranging from about 1 residue to about 1,000 residues in length), or carbon-chain linkers (e.g., C6, C12, C18, C24, etc.).

In some embodiments, the linker contains an N-hydroxysuccinimide ester (NHS) group. In some embodiments, the linker contains a maleimide group. In some embodiments, the linker contains an NHS group and a maleimide group. The NHS group of a linker may then react with a primary amine on a nucleotide or other base-pairing moiety, thereby creating a covalent attachment without modifying or destroying the maleimide group. Such a functionalized nucleotide may then be covalently attached to the enzyme by reaction of the maleimide group with a cysteine residue of the enzyme.

Connection of the nucleotide can be achieved by the formation of a disulfide (forming a readily cleavable connection), formation of an amide, formation of an ester, protein-ligand linkage (e.g., biotin-streptavidin linkage), by alkylation (e.g., using a substituted iodoacetamide reagent) or forming adducts using aldehydes and amines or hydrazines.

In some embodiments, the linker contains, e.g., a maltose group, a biotin group, an O2-benzylcytosine group or O2-benzylcytosine derivative, an O6-benzylguanine group, or an O6-benzylguanine derivative. The NHS group of a linker may then react with a primary amine on a nucleotide, thereby creating a covalent attachment without modifying or destroying the maltose group, biotin group, O2-benzylcytosine group or O2-benzylcytosine derivative, O6-benzylguanine group, or O6-benzylguanine derivative. Such a functionalized nucleotide may then be covalently or non-covalently attached to the enzyme by reaction of the maltose group, biotin group, O2-benzylcytosine group or O2-benzylcytosine derivative, O6-benzylguanine group, or O6-benzylguanine derivative with a suitable functional group or binding partner attached to the enzyme.

Branched PEG molecules allow for simultaneous coupling of protein, dye(s), and nucleotide(s), such that multiple aspects of the compositions described herein may be present within a single reagent. Examples of suitable branched PEG molecules include, but are not limited to, PEG molecules comprising at least 4 branches, at least 8 branches, at least 16 branches, or at least 32 branches. Alternatively, it is contemplated that each individual element may be provided separately.

The length of the linker may vary depending on the type of nucleotide (or other base-pairing moiety) and the enzyme (or other nucleic acid binding moiety). In some instances, the enzyme linked nucleotide should have a length effective to allow the nucleotide or nucleotide analog to pair with a complementary nucleotide while precluding incorporation of the nucleotide or nucleotide analog into the 3' end of a polynucleotide. In some instances, the linker length in the enzyme linked nucleotide is different for each different nucleotide or nucleotide analog. In some instances, the length of the linker will be defined as its persistence length, corresponding to the root-mean-square (RMS) distance between the ends of the linker as characterized by dynamic simulations, 2-D trapping experiments, or ab initio calculations based on statistical distributions of polymers in compact, collapsed, or fluid states as required by the solution, suspension, or fluid conditions present. In some instances, a linker may have persistence length from 0.1 to 1,000 nm, from 0.6 to 500 nm, for from 0.6 to 400 nm. In some instances, a linker may have a persistence length of 0.6, 3.1, 12.7, 22.3, 31.8, 47.7, 95.5, 190.9, 381.8, 763.8 nm, or 989.5 nm or a range defined by or comprising any two or more of these values. In some instances, a linker may have a persistence length of at least 0.1, at least 0.2, at least 0.4, at least 1, at least 2, at least 4, at least 10, at least 20, at least 30, at least 40, at least 50, at least 60, at least 80, at least 90, at least 100, at least 200, at least 300, at least 400, at least 500, at least 700, or at least 1,000 nm, or a persistence length in a range defined by or comprising any two or more of these values. In some instances, linkers provided for one nucleotide may be longer or shorter than the linker provided for another nucleotide. For example, in some instances, dTTP may be linked to a nucleic acid binding moiety thought a longer linker than is used to tether dGTP, or vice versa.

In some instances, a linker for connecting the nucleotide to the enzyme can have a persistence length of about 0.1-1,000 nm, 0.5-500 nm, 0.5-400 nm, 0.5-300 nm, 0.5-200 nm, 0.5-100 nm, 0.5-50 nm, 0.6-500 nm, 0.6-400 nm, 0.6-300 nm, 0.6-200 nm, 0.6-100 nm, 0.6 -50 nm, 1-500 nm, 1-400 nm, 1-300 nm, 1-200 nm, 1-100 nm, 1.5-500 nm, 1.5-400 nm, 1.5-300 nm, 1.5-200 nm, 1.5-100 nm, 1.5-50 nm, 1-50 nm, 5-500 nm, 5-400 nm, 5-300 nm, 5-200 nm, 5-100 nm, or 5-50 nm. In some instances, a linker may have a persistence length of about 0.1, 0.5, 0.6, 1.0, 1.5, 1.8, 2.0, 2.5, 3.0, 3.1, 4.0, 5.0, 6.0, 7.0, 8.0, 9.0, 10.0, 12.7, 22.3, 31.8, 47.7, 95.5, 190.9, or 381.8 nm, or a persistence length in a range defined by or comprising any two or more of these values. In some instances, a linker may have a persistence length of greater than about 0.1, 0.5, 0.6, 1.0, 1.5, 1.8, 2.0, 2.5, 3.0, 3.1, 4.0, 5.0, 6.0, 7.0, 8.0, 9.0, 10.0, 12.7, 22.3, 31.8, 47.7, 95.5, 190.9, or 381.8 nm. In some instances, the linker may have a persistence length of shorter than about 5, 10, 20, 30, 40, 50, 60, 80, 100, 200, 300, 400, 500, 700, or 1,000 nm. In some instances, a linker may have a persistence length of 0.1, 0.2, 0.4, 1, 2, 4, 10, 20, 30, 40, 50, 60, 80, 100, 200, 300, 400, 500, 700, or 1,000 nm, or a persistence length in a range defined by or comprising any two or more of these values.

The polymerase molecules of the disclosure can be site-specifically conjugated to a terminal phosphate group of a nucleoside to form a tethered molecule via a chemical linker. In some embodiments, the chemical linker is an acid-labile linker. In some embodiments, the chemical linker is a base-labile linker. In some embodiments, the chemical linker can be cleaved with irradiation. In some embodiments, the chemical linker can be cleaved with an enzyme, for example, a peptidase, or esterase. In some embodiments, the chemical linker is a pH-sensitive linker. In some embodiments, the chemical linker is an amine-to-thiol crosslinker, such as PEG4-SPDP. In some embodiments, the chemical linker is a thiomaleamic acid linker. In some embodiments, the chemical linker is a silane. In some embodiments, the chemical linker is cleavable using pH or fluoride.

The polymerase chemically linked to the nucleotide can be cleaved using a chemical reagent. In some embodiments, the chemical linker is a disulfide bond, which can be cleaved by a reducing agent. In some embodiments, a disulfide chemical linker is cleaved using β-mercaptoethanol (βME). In some embodiments, the chemical linker is a base-cleavable bond, such as an ester (e.g., succinate). In some embodiments, the chemical linker is a base-cleavable linker that can be cleaved using ammonia or trimethylamine. In some embodiments, the chemical linker is a quaternary ammonium salt that can be cleaved using diisopropylamine.

In some embodiments, the chemical linker is a urethane that can be cleaved by a base, such as aqueous sodium hydroxide.

In some embodiments, the chemical linker is an acid-cleavable linker. In some embodiments, the chemical linker is a benzyl alcohol derivative. In some embodiments, the acid-cleavable linker can be cleaved using trifluoroacetic acid. In some embodiments, the chemical linker teicoplanin aglycone, which can be cleaved by treatment with trifluoroacetic acid and a base. In some embodiments, the chemical linker is an acetal or thioacetal, which can be cleaved by trifluoroacetic acid. In some embodiments, the chemical linker is a thioether that can be cleaved by hydrogen fluoride or cresol. In some embodiments, the chemical linker is a sulfonyl group that can be cleaved by trifluoromethane sulfonic acid, trifluoroacetic acid, or thioanisole. In some embodiments, the chemical linker comprises a nucleophile-cleavable site, such as a phthalimide that can be cleaved by treatment with a hydrazine. In some embodiments, the chemical linker can be an ester that can be cleaved with aluminum trichloride.

In some embodiments, the chemical linker is a Weinreb amide, which can be cleaved by lithium aluminum hydroxide). In some embodiments, the chemical linker is a phosphorothionate that can be cleaved by silver or mercury ions. In some embodiments, the chemical linker can be a diisopropyldialkoxysilyl group that can be cleaved by fluoride ions. In some embodiments, the chemical linker can be a diol that can be cleaved by sodium periodate. In some embodiments, the chemical linker can be an azobenzene that can be cleaved by sodium dithionate.

In some embodiments, the chemical linker is a photo-cleavable linker. In some embodiments, the photo-cleavable linker is an orthonitrobenzyl-based linker, phenacyl linker, alkoxybenzoin linker, chromium arene complex linker, NpSSMpact linker, or pivaloylglycol linker. In some embodiments, the photo-cleavable linker can be cleaved by irradiating the linker at about 365 nm. In some embodiments, the photo-cleavable linker can be cleaved by irradiating the linker at about 405 nm.

In some embodiments, the chemical linker is selected from the group consisting of a silyl linker, an alkyl linker, a polyether linker, a polysulfonyl linker, a polysulfoxide linker, and any combination thereof.

In some embodiments, the linker is cleaved by an enzyme. In some embodiments, the enzyme is a protease, an esterase, a glycosylase, or a peptidase. In some embodiments, the cleaving enzyme breaks bonds in the polymerase. In some embodiments, the cleaving enzyme directly cleaves the linked nucleoside.

Provided herein are methods for enzymatically synthesizing polynucleotides comprising using various buffers. The buffers, in some embodiments, are used in a coupling reaction, deblocking reaction, washing solution, or combinations thereof. In some embodiments, the buffer comprises sodium cacodylate, Tris-HCl, $MgCl_2$, $ZnSO_4$, sodium acetate, or combinations thereof.

The enzymatic methods described herein can be used to synthesize biopolymers. Biopolymers include, but are not limited to, polynucleotides or oligonucleotides. Polynucleotide sequences described herein may be, unless stated otherwise, comprise DNA or RNA. In some cases, the polynucleotide comprises RNA. In some instances, RNA comprises short interfering RNA (siRNA), short hairpin RNA (shRNA), microRNA (miRNA), double-stranded RNA (dsRNA), transfer RNA (tRNA), ribosomal RNA (rRNA), or heterogeneous nuclear RNA (hnRNA). In some instances, RNA comprises shRNA. In some instances, RNA comprises miRNA. In some instances, RNA comprises dsRNA. In some instances, RNA comprises tRNA. In some instances, RNA comprises rRNA. In some instances, RNA comprises hnRNA. In some instances, the polynucleotide is a phosphorodiamidate morpholino oligomers (PMO), which are short single-stranded polynucleotide analogs that are built upon a backbone of morpholine rings connected by phosphorodiamidate linkages. In some instances, the RNA comprises siRNA. In some instances, the polynucleotide comprises siRNA.

In some embodiments, the polynucleotide is from about 8 to about 50 nucleotides in length. In some embodiments, the polynucleotide is from about 10 to about 50 nucleotides in length. In some instances, the polynucleotide is from about 10 to about 30, from about 15 to about 30, from about 18 to about 25, form about 18 to about 24, from about 19 to about 23, or from about 20 to about 22 nucleotides in length.

In some embodiments, the polynucleotide is about 50 nucleotides in length. In some instances, the polynucleotide is about 45 nucleotides in length. In some instances, the polynucleotide is about 40 nucleotides in length. In some instances, the polynucleotide is about 35 nucleotides in length. In some instances, the polynucleotide is about 30 nucleotides in length. In some instances, the polynucleotide is about 25 nucleotides in length. In some instances, the polynucleotide is about 20 nucleotides in length. In some instances, the polynucleotide is about 19 nucleotides in length. In some instances, the polynucleotide is about 18 nucleotides in length. In some instances, the polynucleotide is about 17 nucleotides in length. In some instances, the polynucleotide is about 16 nucleotides in length. In some instances, the polynucleotide is about 15 nucleotides in length. In some instances, the polynucleotide is about 14 nucleotides in length. In some instances, the polynucleotide is about 13 nucleotides in length. In some instances, the polynucleotide is about 12 nucleotides in length. In some instances, the polynucleotide is about 11 nucleotides in length. In some instances, the polynucleotide is about 10 nucleotides in length. In some instances, the polynucleotide is about 8 nucleotides in length. In some instances, the polynucleotide is between about 8 and about 50 nucleotides in length. In some instances, the polynucleotide is between about 10 and about 50 nucleotides in length. In some instances, the polynucleotide is between about 10 and about 45 nucleotides in length. In some instances, the polynucleotide is between about 10 and about 40 nucleotides in length. In some instances, the polynucleotide is between about 10 and about 35 nucleotides in length. In some instances, the polynucleotide is between about 10 and about 30 nucleotides in length. In some instances, the polynucleotide is between about 10 and about 25 nucleotides in length. In some instances, the polynucleotide is between about 10 and about 20 nucleotides in length. In some instances, the polynucleotide is between about 15 and about 25 nucleotides in length. In some instances, the polynucleotide is between about 15 and about 30 nucleotides in length. In some instances, the polynucleotide is between about 12 and about 30 nucleotides in length.

In some embodiments, the DNA or RNA is chemically modified. In some embodiments, the polynucleotide comprises natural or synthetic or artificial nucleotide analogues or bases. In some cases, the polynucleotide comprises combinations of DNA, RNA and/or nucleotide analogues. The polynucleotides may be modified using LNA monomers. In some embodiments, the polynucleotides are modified using MOE, ANA, FANA, PS, or combinations thereof.

In some instances, the synthetic or artificial nucleotide analogues or bases comprise modifications at one or more of ribose moiety, phosphate moiety, nucleoside moiety, or a combination thereof. In some embodiments, nucleotide analogues or artificial nucleotide base comprise a nucleic acid with a modification at a 2' hydroxyl group of the ribose moiety. In some instances, the modification includes an H, OR, R, halo, SH, SR, NH2, NHR, NR2, or CN, wherein R is an alkyl moiety. Exemplary alkyl moiety includes, but is not limited to, halogens, sulfurs, thiols, thioethers, thioesters, amines (primary, secondary, or tertiary), amides, ethers, esters, alcohols and oxygen. In some instances, the alkyl moiety further comprises a modification. In some instances, the modification comprises an azo group, a keto group, an aldehyde group, a carboxyl group, a nitro group, a nitroso, group, a nitrile group, a heterocycle (e.g., imidazole, hydrazino or hydroxylamino) group, an isocyanate or cyanate group, or a sulfur containing group (e.g., sulfoxide, sulfone, sulfide, and disulfide). In some instances, the alkyl moiety further comprises a hetero substitution. In some instances, the carbon of the heterocyclic group is substituted by a nitrogen, oxygen or sulfur. In some instances, the heterocyclic substitution includes but is not limited to, morpholino, imidazole, and pyrrolidino.

Modified polynucleotides may also contain one or more substituted sugar moieties. In some embodiments, the modified polynucleotide comprises one of the following at the 2' position: OH; F; O-, S-, or N-alkyl; O-, S-, or N-alkenyl; O-, S-or N-alkynyl; or O alkyl-O-alkyl, wherein the alkyl, alkenyl and alkynyl may be substituted or unsubstituted C to CO alkyl or $C_2$ to $C_{10}$ alkenyl and alkynyl. Particularly preferred are O (CH2)n OmCH3, O(CH2)n,OCH3, O(CH2) nNH2, O(CH2)nCH3, O(CH2)nONH2, and O(CH2)nON(CH3)2 where n and m can be from 1 to about 10. In some embodiments, the modified polynucleotide comprises one of the following at the 2' position: C to CO, (lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of a polynucleotide, or a group for improving the pharmacodynamic properties of a polynucleotide, and other substituents having similar properties. In some embodiments, modification comprises 2'-methoxyethoxy (2'-O-CH2CH2OCH3, also known as 2'-O-(2- methoxyethyl) or 2'-MOE) i.e., an alkoxyalkoxy group. A further preferred modification comprises 2'-dimethylaminooxyethoxy, i.e. , a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O-CH2-O-CH2-N(CH2)2.

In some embodiments, the polynucleotide one or more of the artificial nucleotide analogues described herein. In some instances, the polynucleotide comprises 1, 2, 3, 4, 5, 6, 7, 8, 9, 10, 11, 12, 13, 14, 15, 16, 17, 18, 20, 25, or more of the artificial nucleotide analogues described herein. In some embodiments, the artificial nucleotide analogues include 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O-N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the polynucleotide comprises 1, 2, 3, 4, 5, 6, 7, 8, 9, 10, 11, 12, 13, 14, 15, 16, 17, 18, 20, 25, or more of the artificial nucleotide analogues selected from 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O-N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the polynucleotide comprises 1, 2, 3, 4, 5, 6, 7, 8, 9, 10, 11, 12, 13, 14, 15, 16, 17, 18, 20, 25, or more of 2'-O-methyl modified nucleotides. In some instances, the polynucleotide comprises 1, 2, 3, 4, 5, 6, 7, 8, 9, 10, 11, 12, 13, 14, 15, 16, 17, 18, 20, 25, or more of 2'-O-methoxyethyl (2'-O-MOE) modified nucleotides. In some instances, the polynucleotide comprises 1, 2, 3, 4, 5, 6, 7, 8, 9, 10, 11, 12, 13, 14, 15, 16, 17, 18, 20, 25, or more of thiolphosphonate nucleotides.

In some embodiments, the modifications comprise 2'-methoxy (2'-O CH3), 2'-aminopropoxy (2'-O CH2CH2CH2NH2) and 2'-fluoro (2'-F). Similar modifications may also be made at other positions on the polynucleotide, particularly the 3' position of the sugar on the 3' terminal nucleotide or in 2'-5' linked polynucleotides and the 5' position of 5' terminal nucleotide. In some embodiments, the polynucleotide comprises sugar mimetics such as cyclobutyl moieties in place of the pentofuranosyl sugar.

Polynucleotides may also comprise nucleobase ("base") modifications or substitutions. As used herein, "unmodified" or "natural" nucleotides comprise the purine bases adenine (A) and guanine (G), and the pyrimidine bases thymine (T), cytosine (C) and uracil (U). Modified nucleotides comprise other synthetic and natural nucleotides such as 5-methylcytosine (5-me-C), 5-hydroxymethyl cytosine, xanthine, hypoxanthine, 2- aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

In some embodiments, the polynucleotide backbone is modified. In some embodiments, the polynucleotide backbone comprises, but not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

In some embodiments, the modified polynucleotide backbone does not comprise a phosphorus atom therein and comprise backbones that are formed by short chain alkyl or cycloalkyl intemucleoside linkages, mixed heteroatom and alkyl or cycloalkyl intemucleoside linkages, or one or more short chain heteroatomic or heterocyclic intemucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

In some embodiments, the polynucleotide is modified by chemically linking the polynucleotide to one or more moieties or conjugates. Exemplary moieties include, but are not limited to, lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or Adamantane acetic acid, a palmityl moiety, or an octadecylamine or hexylamino-carbonyl-t oxycholesterol moiety.

When a non-naturally occurring chemical linker is cleaved from a polynucleotide or polynucleotide, the remaining chemical moiety is referred to as a "scar." In some embodiments, the scar is an olefin or alkyne moiety. The methods as described herein, in some embodiments, do not leave a scar. In some embodiments, no scar remains after the linked phosphate is cleaved.

The method of enzymatic polynucleotide synthesis disclosed herein can have a coupling efficiency of at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, or at least 99.9%. In some embodiments, the method can have a coupling efficiency of at least 99.5%. In some embodiments, the method can have a coupling efficiency of at least 99.7%. In some embodiments, the method can have a coupling efficiency of at least 99.9%.

The method of enzymatic polynucleotide synthesis disclosed herein can have a coupling efficiency of about 95%, about 95.5%, about 96%, about 96.5%, about 97%, about 97.5%, about 98%, about 98.5%, about 99%, about 99.5%, about 99.6%, about 99.7%, about 99.8%, or about 99.9%. In some embodiments, the method can have a coupling efficiency of about 99.5%. In some embodiments, the method can have a coupling efficiency of about 99.7%. In some embodiments, the method can have a coupling efficiency of about 99.9%.

The method of enzymatic polynucleotide synthesis described herein can have a total average error rate of less than about 1 in 100, less than about 1 in 200, less than about 1 in 300, less than about 1 in 400, less than about 1 in 500, less than about 1 in 1000, less than about 1 in 2000, less than about 1 in 5000, less than about 1 in 10000, less than about 1 in 15000, or less than about 1 in 20000 bases. In some embodiments, the total average error rate is less than about 1 in 100. In some embodiments, the total average error rate is less than about 1 in 200. In some embodiments, the total average error rate is less than about 1 in 500. In some embodiments, the total average error rate is less than about 1 in 1000.

The method of enzymatic polynucleotide synthesis described herein can have a total average error rate of less than about 95%, less than about 96%, less than about 97%, less than about 98%, less than about 99%, less than about 99.5%, less than about 99.6%, less than about 99.7%, less than about 99.8%, or less than about 99.9%. In some embodiments, the method can have a total average error rate of less than about 99.5%. In some embodiments, the method can have a total average error rate of less than about 99.7%. In some embodiments, the method can have a total average error rate of less than about 99.9%.

The error rates of the method disclosed herein are for at least 50%, 60%, 70%, 80%, 90%, 95%, 98%, 99%, 99.5%, or more of the polynucleotides synthesized. In some embodiments, the error rates are for at least 60% of the synthesized polynucleotides. In some embodiments, the error rates are for at least 80% of the synthesized polynucleotides. In some embodiments, the error rates are for at least 90% of the synthesized polynucleotides. In some embodiments, the error rates are for at least 99% of the synthesized polynucleotides. Individual types of error rates include mismatches, deletions, insertions, and/or substitutions for the polynucleotides synthesized on the substrate. The term "error rate" refers to a comparison of the collective amount of synthesized biopolymer to an aggregate of predetermined biopolymer sequence.

The method of enzymatic polynucleotide synthesis disclosed herein can extend a primer by a single nucleotide in from about 1 second (sec) to about 20 sec. In some embodiments, the method can extend a single nucleotide in from about 1 sec to about 5 sec. In some embodiments, the method can extend a single nucleotide in from about 5 sec to about 10 sec. In some embodiments, the method can extend a single nucleotide in from about 10 sec to about 15 sec. In some embodiments, the method can extend a single nucleotide in from about 15 sec to about 20 sec. In some embodiments, the method can extend a single nucleotide in from about 10 sec to about 20 sec.

The method of enzymatic polynucleotide synthesis disclosed herein can extend a primer by a single nucleotide in about 1 second (sec), about 2 sec, about 3 sec, about 4 sec, about 5 sec, about 6 sec, about 7 sec, about 8 sec, about 9 sec, about 10 sec, about 11 sec, about 12 sec, about 13 sec, about 14 sec, about 15 sec, about 16 sec, about 17 sec, about 18 sec, about 19 sec, or about 20 sec. In some embodiments, the method can extend a single nucleotide in about 5 sec. In some embodiments, the method can extend a single nucleotide in about 10 sec. In some embodiments, the method can extend a single nucleotide in about 15 sec. In some embodiments, the method can extend a single nucleotide in about 20 sec.

The method of enzymatic polynucleotide synthesis disclosed herein can extend a polynucleotide by at least about 10 nucleotides per hour. In some instances, the method extends a polynucleotide by at least about 5, 10, 15, 20, 25, 30, 35, 40, 45, 50, or more than 50 nucleotides per hour.

The synthesized polynucleotides of the disclosure can be between about 50 bases to about 1000 bases. In some embodiments, the synthesized polynucleotides comprise at least 10, at least 20, at least 30, at least 40, at least 50, at least 60, at least 70, at least 80, at least 90, at least 100, at least 125, at least 150, at least 175, at least 200, at least 225, at least 250, at least 275, at least 300, at least 325, at least 350, at least 375, at least 400, at least 425, at least 450, at least 475, at least 500, at least 600, at least 700, at least 800, at least 900, at least 1000, at least 1100, at least 1200, at least 1300, at least 1400, at least 1500, at least 1600, at least 1700, at least 1800, at least 1900, or at least 2000 bases. In some embodiments, the synthesized polynucleotides comprise about 10, about 20, about 30, about 40, about 50, about 60, about 70, about 80, about 90, about 100, about 125, about 150, about 175, about 200, about 225, about 250, about 275, about 300, about 325, about 350, about 375, about 400, about 425, about 450, about 475, about 500, about 600, about 700, about 800, about 900, about 1000, about 1100, about 1200, about 1300, about 1400, about 1500, about 1600, about 1700, about 1800, about 1900, about 2000, about 2100, about 2200, about 2300, about 2400, about 2500, about 2600, about 2700, about 2800, about 2900, about 3000, 4000, 5000, or more than 5000 bases.

In some embodiments, the polymerase-nucleotide conjugates can comprise additional moieties that terminate elongation of a nucleic acid once the tethered nucleic acid is incorporated. In some embodiments, a 3' O-modified or base-modified reversible terminator deoxynucleoside triphosphate (RTdNTP) is tethered to the polymerase. In some embodiments, the reversible terminator may be coupled to the oxygen atom of the 3-prime hydroxyl group of the nucleotide pentose (e.g., 3'-O-blocked reversible terminator). Alternatively, or in addition to, the reversible terminator may be coupled to the nucleobase of the nucleotide (e.g., 3'-unblocked reversible terminator). In some embodiments, a reversible terminator nucleotide is a chemically modified nucleoside triphosphate analog that stops elongation once incorporated into the nucleic acid molecule. When a conjugate comprising a polymerase and an RTdNTP is used for the extension of nucleic acids, cleavage of the linker and deprotection of the RTdNTP may be required to enable an extended nucleic acid to undergo further nucleotide addition. The reversible terminator may include a detectable label. The reversible terminator may comprise an allyl, hydroxylamine, acetate, benzoate, phosphate, azidomethyl, or amide group. The reversible terminator may be removed by treatment with a reducing agent, acid or base, organic solvents, ionic surfactants, photons (photolysis), or any combination thereof.

In a conjugate, the linker is considered to be at least the atoms that connect the α-phosphate of a nucleotide to a $C_\alpha$ atom in the backbone of the polymerase. In some embodiments, the polymerase and the nucleotide are covalently linked, and the distance between the linked atom of the nucleotide and the $C_\alpha$ atom in the backbone of the polymerase is from about 4 Å to about 100 Å. In some embodiments, the distance between the linked atom of the nucleoside and the $C_\alpha$ atom in the backbone of the polymerase is about 5 Å to about 20 Å. In some embodiments, the distance between the linked atom of the nucleoside and the $C_\alpha$ atom in the backbone of the polymerase is about 20 Å to about 50 Å. In some embodiments, the distance between the linked atom of the nucleoside and the $C_\alpha$ atom in the backbone of the polymerase is about 50 Å to about 75 Å. In some embodiments, the distance between the linked atom of the nucleoside and the $C_\alpha$ atom in the backbone of the polymerase is about 75 Å to about 100 Å.

In some embodiments, the linker is joined to the base of the nucleotide at an atom that is not involved in base pairing. In some embodiments, the linker is at least the atoms that connect a $C_\alpha$ atom in the backbone of the polymerase to a terminal phosphate group of the nucleotide.

The linker should be sufficiently long to allow the nucleoside triphosphate to access the active site of the polymerase to which it is tethered. The polymerase of a conjugate can catalyze the addition of the nucleotide to which it is linked onto the 3' end of a nucleic acid.

Methods of Use

The compositions and methods described herein can be used in nucleic acid assembly. In some embodiments, the nucleic acid is a DNA. In some embodiments, the nucleic acid is an RNA. In some embodiments, the compositions and methods described herein can be used to assemble nucleic acids that are about 8 to about 50 nucleotides in length. In some embodiments, the compositions and methods described herein can be used to assemble nucleic acids that are about 50 nucleic acids in length.

The compositions and methods described herein can be used in place of Gibson assembly. The compositions and methods described herein can be used to join multiple DNA fragments in a single, isothermal reaction. In some embodiments, the compositions and methods described herein can be used to combine 1, 2, 3, 4, 5, 6, 7, 8, 9, 10, 11, 12, 13, 14, 15, 16, 17, 18 19, or 20 DNA fragments based on sequence identity. In some embodiments, the compositions or methods described herein can be used to combine 10 DNA fragments. In some embodiments, the compositions or methods described herein can be used to combine 15 DNA fragments. In some embodiments, the compositions or methods described herein can be used to combine 20 DNA fragments. In some embodiments, the DNA fragments to be combined contain an about 15, about 20, about 25, about 30, about 35, about 40, about 45, or about 50 base pair overlap with adjacent DNA fragments. In some embodiments, the DNA fragments to be combined using the methods described herein contain an about 20 base pair overlap with adjacent DNA fragments. In some embodiments, the DNA fragments to be combined using the methods described herein contain an about 30 base pair overlap with adjacent DNA fragments. In some embodiments, the DNA fragments to be combined using the methods described herein contain an about 40 base pair overlap with adjacent DNA fragments.

Described herein are compositions and methods for gene assembly to generate a gene library. The gene library can comprise a collection of genes. In some embodiments, the collection comprises at least 100 different preselected synthetic genes that can be of at least 0.5 kb length with an error rate of less than 1 in 3000 bp compared to predetermined sequences comprising the genes. The collection may comprise at least 100 different preselected synthetic genes that can be each of at least 0.5 kb length. At least 90% of the preselected synthetic genes may comprise an error rate of less than 1 in 3000 bp compared to predetermined sequences comprising the genes. Desired predetermined sequences may be supplied by any method, typically by a user, e.g. a user entering data using a computerized system. In various embodiments, synthesized nucleic acids are compared against these predetermined sequences, in some cases by sequencing at least a portion of the synthesized nucleic acids, e.g. using next-generation sequencing methods. In some embodiments related to any of the gene libraries described herein, at least 90% of the preselected synthetic genes comprise an error rate of less than 1 in 5000 bp compared to predetermined sequences comprising the genes. In some embodiments, at least 0.05% of the preselected genes are error free. In some embodiments, at least 0.5% of the preselected genes are error free. In some embodiments, at least 90% of the preselected genes comprise an error rate of less than 1 in 3000 bp compared to predetermined sequences comprising the genes. In some embodiments, at least 90% of the preselected genes are error free or substantially error free. In some embodiments, the preselected genes comprise a deletion rate of less than 1 in 3000 bp compared to predetermined sequences comprising the genes. In some embodiments, the preselected genes comprise an insertion rate of less than 1 in 3000 bp compared to predetermined sequences comprising the genes. In some embodiments, the preselected genes comprise a substitution rate of less than 1 in 3000 bp compared to predetermined sequences comprising the genes. In some embodiments, the gene library as described herein further comprises at least 10 copies of each gene. In some embodiments, the gene library as described herein further comprises at least 100 copies of each gene. In some embodiments, the gene library as described herein further comprises at least 1000 copies of each gene. In some embodiments, the gene library as described herein further comprises at least 1000000 copies of each gene. In some embodiments, the collection of genes as described herein comprises at least 500 genes. In some embodiments, the collection comprises at least 5000 genes. In some embodiments, the collection comprises at least 10000 genes. In some embodiments, the preselected genes are at least 1 kb. In some embodiments, the preselected genes are at least 2 kb. In some embodiments, the preselected genes are at least 3 kb. In some embodiments, the predetermined sequences comprise less than 20 bp in addition compared to the preselected genes. In some embodiments, the predetermined sequences comprise less than 15 bp in addition compared to the preselected genes. In some embodiments, at least one of the genes differs from any other gene by at least 0.1%. In some embodiments, each of the genes differs from any other gene by at least 0.1%. In some embodiments, at least one of the genes differs from any other gene by at least 10%. In some embodiments, each of the genes differs from any other gene by at least 10%. In some embodiments, at least one of the genes differs from any other gene by at least 2 base pairs. In some embodiments, each of the genes differs from any other gene by at least 2 base pairs. In some embodiments, the gene library as described herein further comprises genes that are of less than 2 kb with an error rate of less than 1 in 20000 bp compared to preselected sequences of the genes. In some embodiments, a subset of the deliverable genes is covalently linked together. In some embodiments, a first subset of the collection of genes encodes for components of a first metabolic pathway with one or more metabolic end products. In some embodiments, the gene library as described herein further comprises selecting of the one or more metabolic end products, thereby constructing the collection of genes. In some embodiments, the one or more metabolic end products comprise a biofuel. In some embodiments, a second subset of the collection of genes encodes for components of a second metabolic pathway with one or more metabolic end products. In some embodiments, the gene library is in a space that is less than 100 m3. In some embodiments, the gene library is in a space that is less than 1 m3.

In some instances, described herein are methods of constructing a gene library. The method may comprise the steps of: entering before a first timepoint, in a computer readable non-transient medium at least a first list of genes and a second list of genes, wherein the genes are at least 500 bp and when compiled into a joint list, the joint list comprises at least 100 genes; synthesizing more than 90% of the genes in the joint list before a second timepoint, thereby constructing a gene library with deliverable genes. In some embodiments, the second timepoint is less than a month apart from the first timepoint.

In practicing any of the methods of constructing a gene library as provided herein, the method as described herein further comprises delivering at least one gene at a second timepoint. In some embodiments, at least one of the genes differs from any other gene by at least 0.1% in the gene library. In some embodiments, each of the genes differs from any other gene by at least 0.1% in the gene library. In some embodiments, at least one of the genes differs from any other gene by at least 10% in the gene library. In some embodiments, each of the genes differs from any other gene by at least 10% in the gene library. In some embodiments, at least one of the genes differs from any other gene by at least 2 base pairs in the gene library. In some embodiments, each of the genes differs from any other gene by at least 2 base pairs in the gene library. In some embodiments, at least 90% of the deliverable genes are error free. In some embodiments, the deliverable genes comprises an error rate of less than 1/3000 resulting in the generation of a sequence that deviates from the sequence of a gene in the joint list of genes. In some embodiments, at least 90% of the deliverable genes comprise an error rate of less than 1 in 3000 bp resulting in the generation of a sequence that deviates from the sequence of a gene in the joint list of genes. In some embodiments, genes in a subset of the deliverable genes are covalently linked together. In some embodiments, a first subset of the joint list of genes encode for components of a first metabolic pathway with one or more metabolic end products. In some embodiments, any of the methods of constructing a gene library as described herein further comprises selecting of the one or more metabolic end products, thereby constructing the first, the second or the joint list of genes. In some embodiments, the one or more metabolic end products comprise a biofuel. In some embodiments, a second subset of the joint list of genes encode for components of a second metabolic pathway with one or more metabolic end products. In some embodiments, the joint list of genes comprises at least 500 genes. In some embodiments, the joint list of genes comprises at least 5000 genes. In some embodiments, the joint list of genes comprises at least 10000 genes. In some embodiments, the genes can be at least 1 kb. In some embodiments, the genes are at least 2 kb. In some embodiments, the genes are at least 3 kb. In some embodiments, the second timepoint is less than 25 days apart from the first timepoint. In some embodiments, the second timepoint is less than 5 days apart from the first timepoint. In some embodiments, the second timepoint is less than 2 days apart from the first timepoint. It is noted that any of the embodiments described herein can be combined with any of the methods, devices or systems provided in the current disclosure.

In another aspect, a method of constructing a gene library is provided herein. The method comprises the steps of: entering at a first timepoint, in a computer readable non-transient medium a list of genes; synthesizing more than 90% of the list of genes, thereby constructing a gene library with deliverable genes; and delivering the deliverable genes at a second timepoint. In some embodiments, the list comprises at least 100 genes and the genes can be at least 500 bp. In still yet some embodiments, the second timepoint is less than a month apart from the first timepoint.

In practicing any of the methods of constructing a gene library as provided herein, in some embodiments, the method as described herein further comprises delivering at least one gene at a second timepoint. In some embodiments, at least one of the genes differs from any other gene by at least 0.1% in the gene library. In some embodiments, each of the genes differs from any other gene by at least 0.1% in the gene library. In some embodiments, at least one of the genes differs from any other gene by at least 10% in the gene library. In some embodiments, each of the genes differs from any other gene by at least 10% in the gene library. In some embodiments, at least one of the genes differs from any other gene by at least 2 base pairs in the gene library. In some embodiments, each of the genes differs from any other gene by at least 2 base pairs in the gene library. In some embodiments, at least 90% of the deliverable genes are error free. In some embodiments, the deliverable genes comprises an error rate of less than 1/3000 resulting in the generation of a sequence that deviates from the sequence of a gene in the list of genes. In some embodiments, at least 90% of the deliverable genes comprise an error rate of less than 1 in 3000 bp resulting in the generation of a sequence that deviates from the sequence of a gene in the list of genes. In some embodiments, genes in a subset of the deliverable genes are covalently linked together. In some embodiments, a first subset of the list of genes encode for components of a first metabolic pathway with one or more metabolic end products. In some embodiments, the method of constructing a gene library further comprises selecting of the one or more metabolic end products, thereby constructing the list of genes. In some embodiments, the one or more metabolic end products comprise a biofuel. In some embodiments, a second subset of the list of genes encode for components of a second metabolic pathway with one or more metabolic end products. It is noted that any of the embodiments described herein can be combined with any of the methods, devices or systems provided in the present disclosure.

In practicing any of the methods of constructing a gene library as provided herein, in some embodiments, the list of genes comprises at least 500 genes. In some embodiments, the list comprises at least 5000 genes. In some embodiments, the list comprises at least 10000 genes. In some embodiments, the genes are at least 1 kb. In some embodiments, the genes are at least 2 kb. In some embodiments, the genes are at least 3 kb. In some embodiments, the second timepoint as described in the methods of constructing a gene library is less than 25 days apart from the first timepoint. In some embodiments, the second timepoint is less than 5 days apart from the first timepoint. In some embodiments, the second timepoint is less than 2 days apart from the first timepoint. It is noted that any of the embodiments described herein can be combined with any of the methods, devices or systems provided in the present disclosure.

Figure 3:
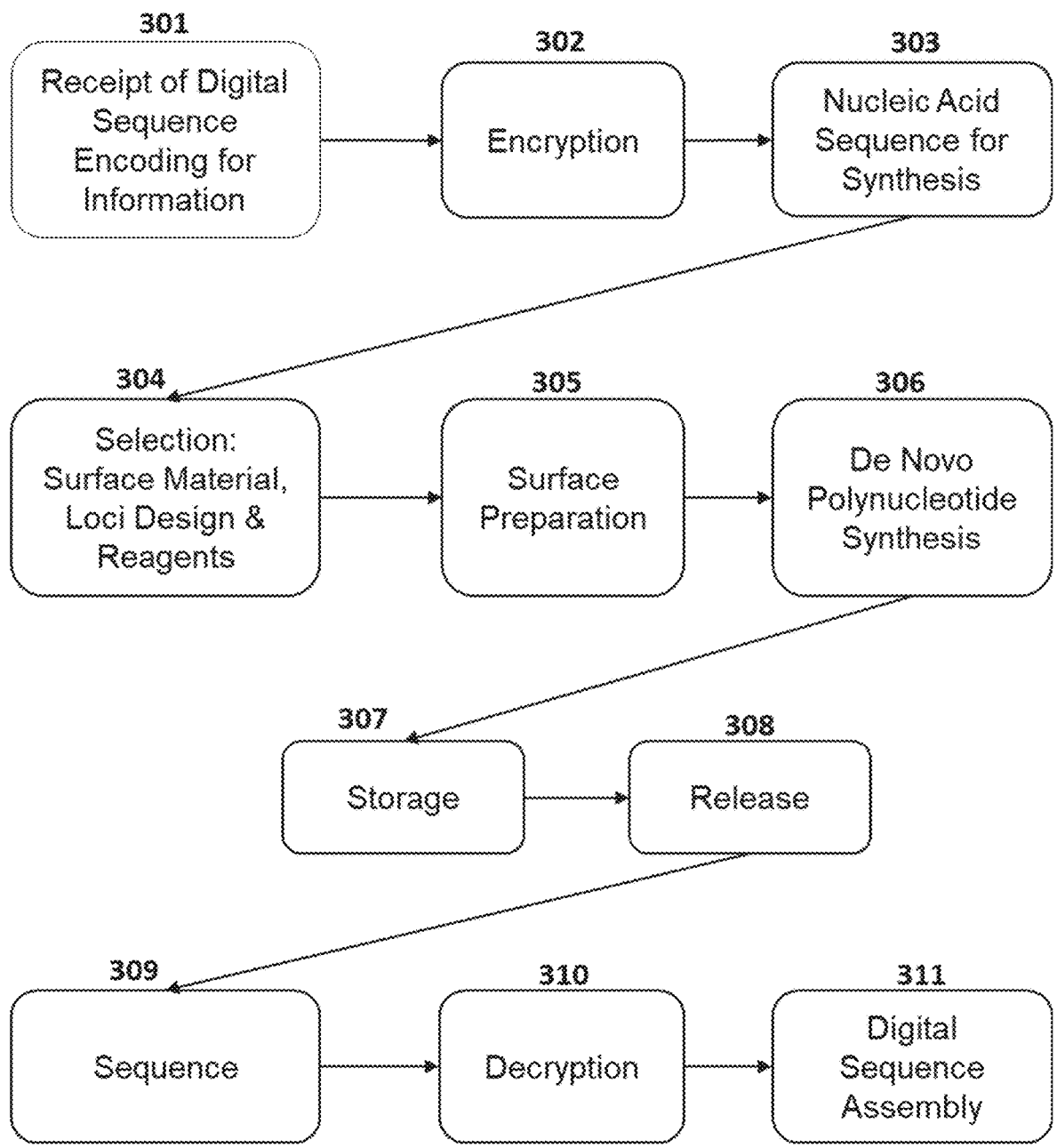
FIG. 3 illustrates an exemplary workflow for nucleic acid-based information storage.

The compositions and methods descried herein can be used for DNA digital data storage. In some embodiments, the compositions and methods disclosed herein can be used to prepare DNA molecules for four bit information coding. An exemplary workflow is provided in FIG. 3. In a first step, a digital sequence encoding an item of information (i.e., digital information in a binary code for processing by a computer) is received 301. An encryption 302 scheme is applied to convert the digital sequence from a binary code to a nucleic acid sequence 303. A surface material for nucleic acid extension, a design for loci for nucleic acid extension (aka, arrangement spots), and reagents for nucleic acid synthesis are selected 304. The surface of a structure is prepared for nucleic acid synthesis 305. De novo polynucleotide synthesis is performed 306. The synthesized polynucleotides are stored 307 and available for subsequent release 308, in whole or in part. Once released, the polynucleotides, in whole or in part, are sequenced 309, subject to decryption 310 to convert nucleic sequence back to digital sequence. The digital sequence is then assembled 311 to obtain an alignment encoding for the original item of information.

Computer Systems

Any of the systems described herein, may be operably linked to a computer and may be automated through a computer either locally or remotely. In various instances, the methods and systems of the disclosure may further comprise software programs on computer systems and use thereof. Accordingly, computerized control for the synchronization of the dispense/vacuum/refill functions such as orchestrating and synchronizing the material deposition device movement, dispense action and vacuum actuation are within the bounds of the disclosure. The computer systems may be programmed to interface between the user specified base sequence and the position of a material deposition device to deliver the correct reagents to specified regions of the substrate.

Figure 4:
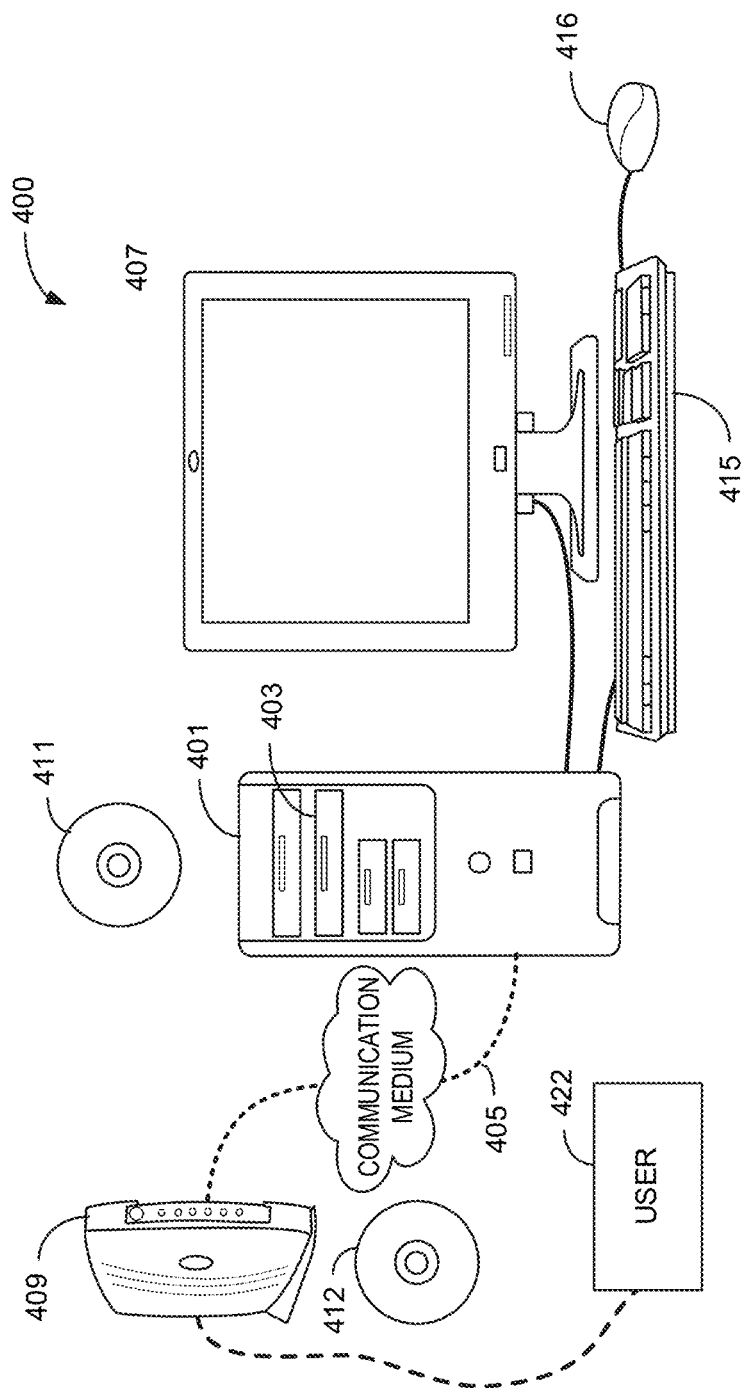
FIG. 4 illustrates an example of a computer system.

The computer system 400 illustrated in FIG. 4 may be understood as a logical apparatus that can read instructions from media 411 and/or a network port 405, which can optionally be connected to server 409 having fixed media 412. The system, such as shown in FIG. 4 can include a CPU 401, disk drives 403, optional input devices such as keyboard 415 and/or mouse 416 and optional monitor 407. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 422 as illustrated in FIG. 4.

Figure 5:
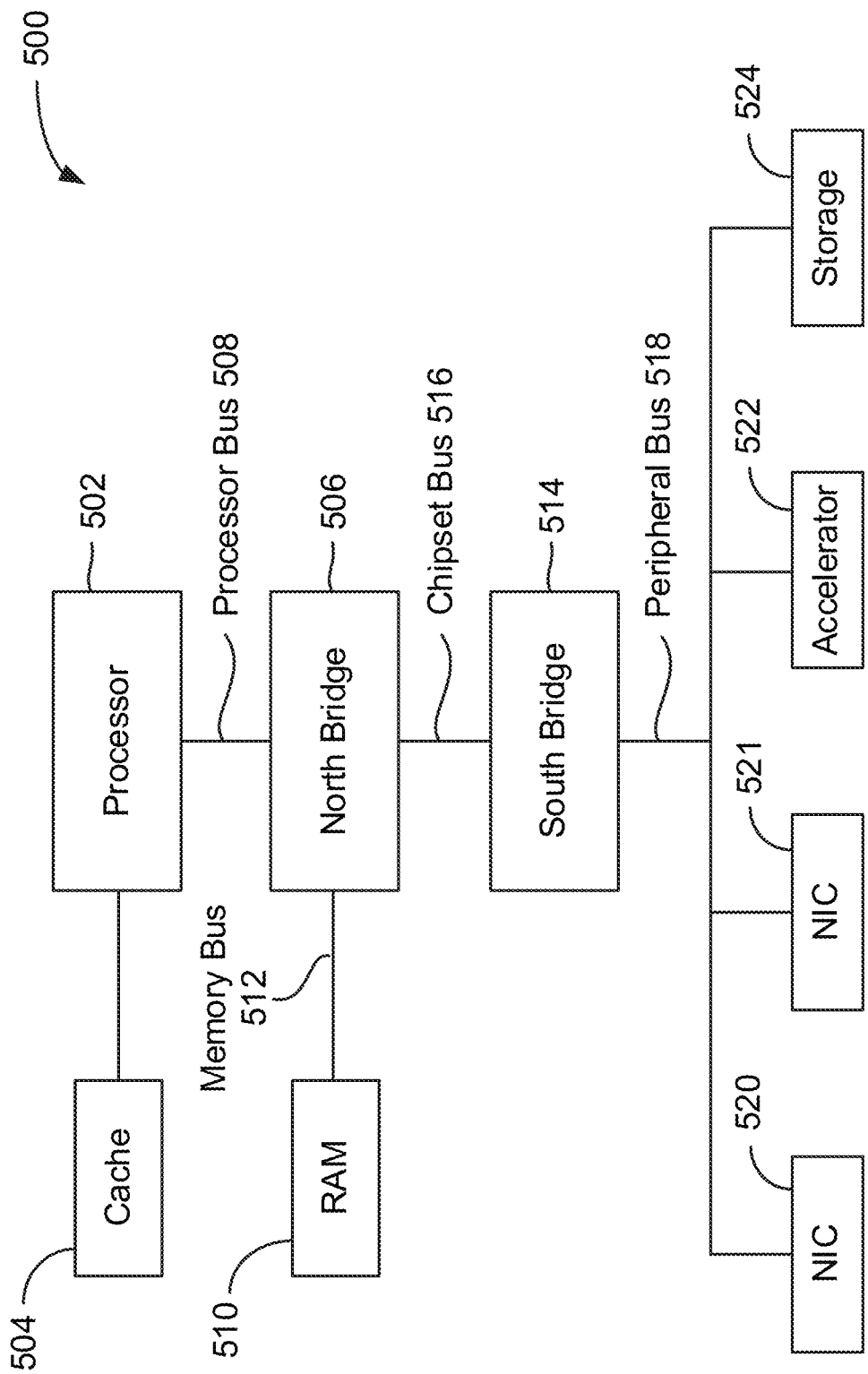
FIG. 5 is a block diagram illustrating an architecture of a computer system.

FIG. 5 is a block diagram illustrating a first example architecture of a computer system 500 that can be used in connection with example instances of the present disclosure. As depicted in FIG. 5, the example computer system can include a processor 502 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some instances, multiple processors or processors with multiple cores can also be used, whether in a single computer system, in a cluster, or distributed across systems over a network comprising a plurality of computers, cell phones, and/or personal data assistant devices.

As illustrated in FIG. 5, a high speed cache 504 can be connected to, or incorporated in, the processor 502 to provide a high speed memory for instructions or data that have been recently, or are frequently, used by processor 502. The processor 502 is connected to a north bridge 506 by a processor bus 508. The north bridge 506 is connected to random access memory (RAM) 510 by a memory bus 512 and manages access to the RAM 510 by the processor 502. The north bridge 506 is also connected to a south bridge 514 by a chipset bus 516. The south bridge 514 is, in turn, connected to a peripheral bus 518. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 518. In some alternative architectures, the functionality of the north bridge can be incorporated into the processor instead of using a separate north bridge chip. In some instances, system 500 can include an accelerator card 522 attached to the peripheral bus 518. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 524 and can be loaded into RAM 510 and/or cache 504 for use by the processor. The system 500 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example instances of the present disclosure. In this example, system 500 also includes network interface cards (NICs) 520 and 521 connected to the peripheral bus for providing network interfaces to external storage, such as Network Attached Storage (NAS) and other computer systems that can be used for distributed parallel processing.

Figure 6:
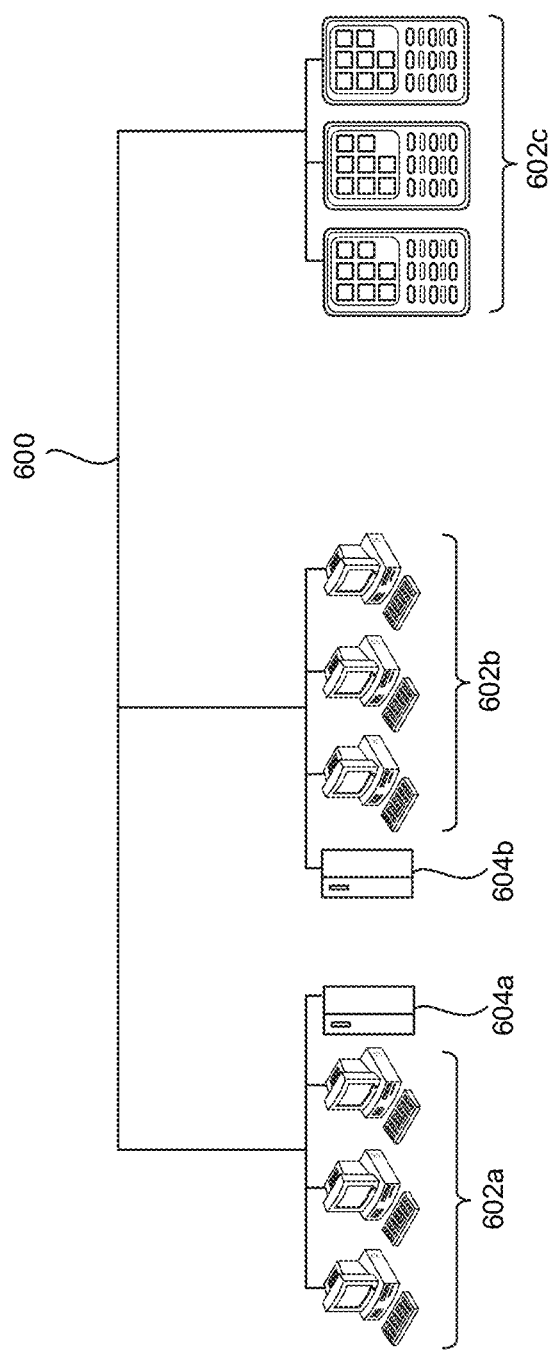
FIG. 6 is a diagram demonstrating a network configured to incorporate a plurality of computer systems, a plurality of cell phones and personal data assistants, and Network Attached Storage (NAS).

FIG. 6 is a diagram showing a network 600 with a plurality of computer systems 602a, and 602b, a plurality of cell phones and personal data assistants 602c, and Network Attached Storage (NAS) 604a, and 604b. In example instances, systems 602a, 602b, and 602c can manage data storage and optimize data access for data stored in Network Attached Storage (NAS) 604a and 604b. A mathematical model can be used for the data and be evaluated using distributed parallel processing across computer systems 602a, and 602b, and cell phone and personal data assistant systems 602c. Computer systems 602a, and 602b, and cell phone and personal data assistant systems 602c can also provide parallel processing for adaptive data restructuring of the data stored in Network Attached Storage (NAS) 604a and 604b. FIG. 6 illustrates an example only, and a wide variety of other computer architectures and systems can be used in conjunction with the various instances of the present disclosure. For example, a blade server can be used to provide parallel processing. Processor blades can be connected through a back plane to provide parallel processing. Storage can also be connected to the back plane or as Network Attached Storage (NAS) through a separate network interface. In some example instances, processors can maintain separate memory spaces and transmit data through network interfaces, back plane or other connectors for parallel processing by other processors. In other instances, some or all of the processors can use a shared virtual address memory space.

Figure 7:
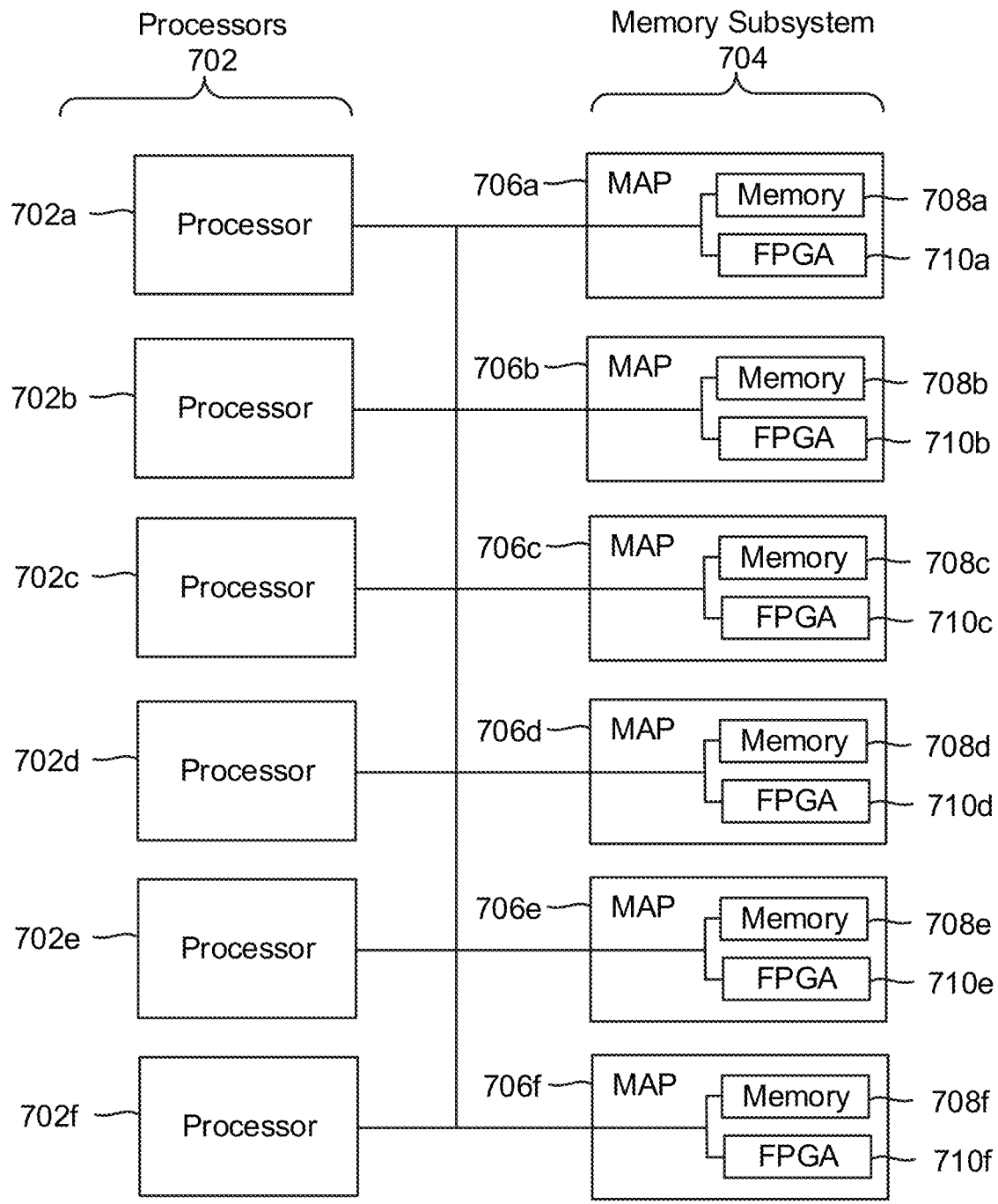
FIG. 7 is a block diagram of a multiprocessor computer system using a shared virtual address memory space.

FIG. 7 is a block diagram of a multiprocessor computer system using a shared virtual address memory space in accordance with an example instance. The system includes a plurality of processors 702a-f that can access a shared memory subsystem 704. The system incorporates a plurality of programmable hardware memory algorithm processors (MAPs) 706a-f in the memory subsystem 704. Each MAP 706a-f can comprise a memory 708a-f and one or more field programmable gate arrays (FPGAs) 710a-f The MAP provides a configurable functional unit and particular algorithms or portions of algorithms can be provided to the FPGAs 710a-f for processing in close coordination with a respective processor. For example, the MAPs can be used to evaluate algebraic expressions regarding the data model and to perform adaptive data restructuring in example instances. In this example, each MAP is globally accessible by all of the processors for these purposes. In one configuration, each MAP can use Direct Memory Access (DMA) to access an associated memory 708a-f, allowing it to execute tasks independently of, and asynchronously from the respective microprocessor 702a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example instances, including systems using any combination of general processors, co-processors, FPGAs and other programmable logic devices, system on chips (SOCs), application specific integrated circuits (ASICs), and other processing and logic elements. In some instances, all or part of the computer system can be implemented in software or hardware. Any variety of data storage media can be used in connection with example instances, including random access memory, hard drives, flash memory, tape drives, disk arrays, Network Attached Storage (NAS) and other local or distributed data storage devices and systems.

In example instances, the computer system can be implemented using software modules executing on any of the above or other computer architectures and systems. In other instances, the functions of the system can be implemented partially or completely in firmware, programmable logic devices such as field programmable gate arrays (FPGAs) as referenced in FIG. 5, system on chips (SOCs), application specific integrated circuits (ASICs), or other processing and logic elements. For example, the Set Processor and Optimizer can be implemented with hardware acceleration through the use of a hardware accelerator card, such as accelerator card 522 illustrated in FIG. 5.

EXAMPLES

The following examples are set forth to illustrate more clearly the principles and practice of embodiments disclosed herein to those skilled in the art and are not to be construed as limiting the scope of any claimed embodiments. Unless otherwise stated, all parts and percentages are on a weight basis.

Example 1: Single Strand Chain Extension Using dN6P Substrates and TdT Enzyme

Figure 8:
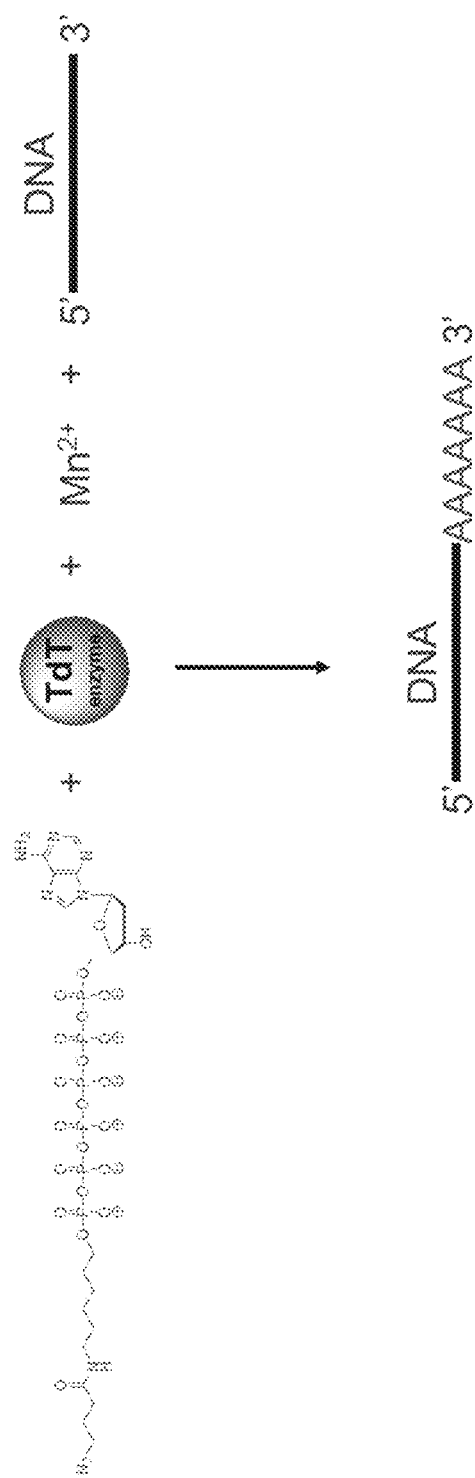
FIG. 8 is an experimental schema of single strand chain extension using dN6P substrates and TdT enzyme.
Figure 9:
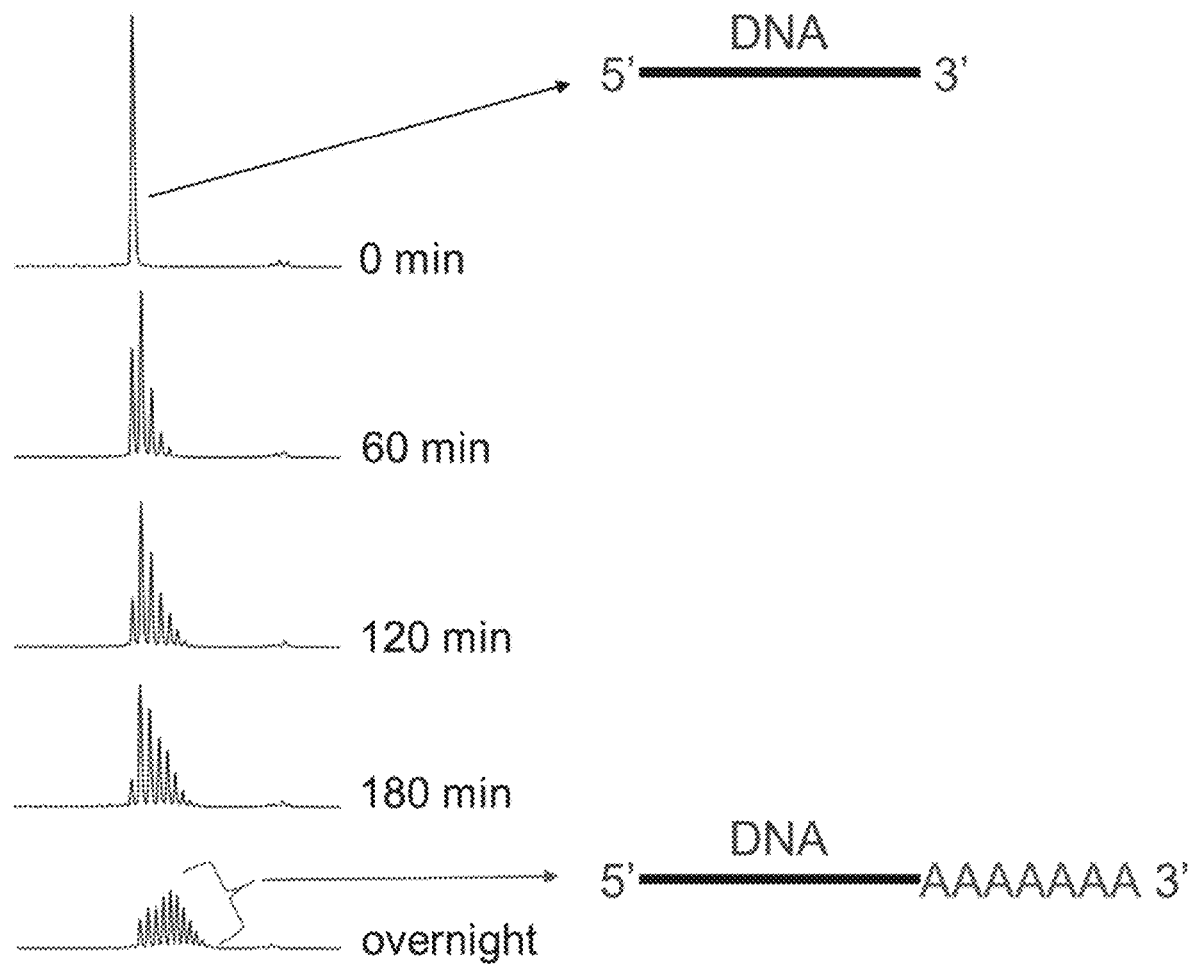
FIG. 9 illustrates HPLC chromatograms of chain extension of dA6P (deoxyadenosine hexaphosphate) substrate by TdT.

TdT was used for single strand extension. Briefly, TdT was incubated with a single stranded DNA, manganese, and dA6P (deoxyadenosine hexaphosphate) substrate. A schema of the reaction is seen in FIG. 8. An HPLC chromatograph (FIG. 9) shows chain extension of dA6P substrate by TdT. No protecting group was used on the 3' end, resulting in multiple additions of dA.

The data shows that TdT can be used for enzymatic based nucleic acid synthesis.

Figure 10A:
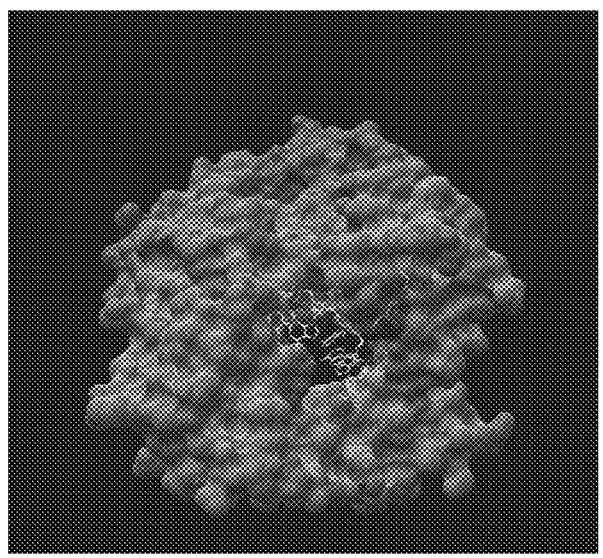
FIG. 10A illustrates TdT bound to polyA ssDNA substrate.
Figure 10B:
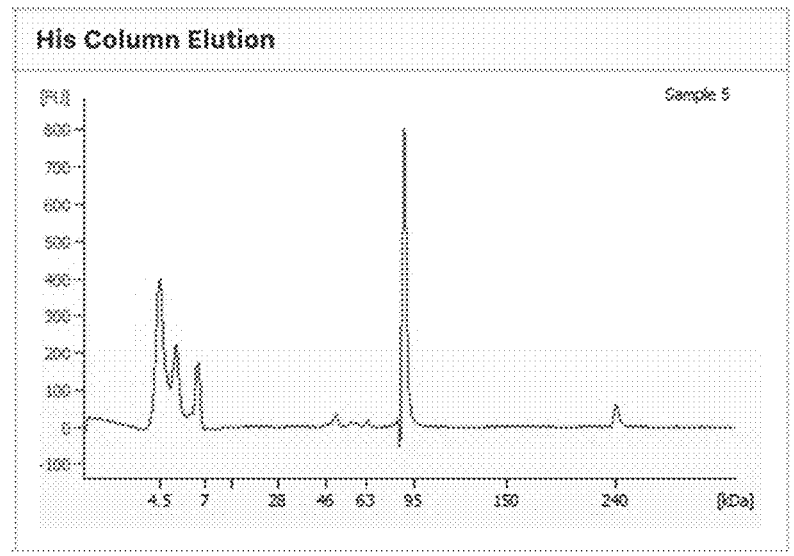
FIG. 10B illustrates expression and purification of NTT-1.
Figure 10C:
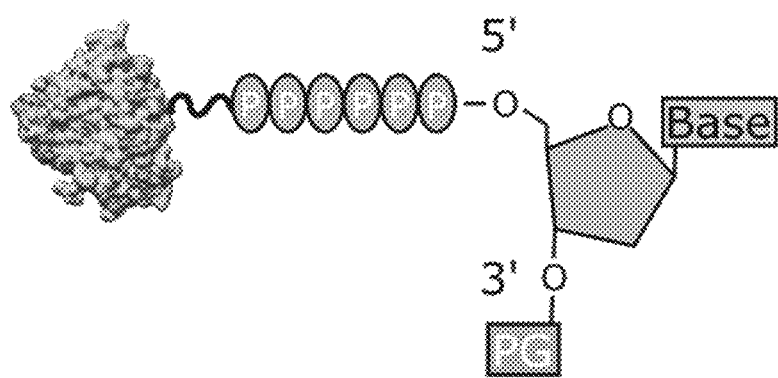
FIG. 10C illustrates a schema of a NTT-TIDE.

Example 2: Single Strand Chain Extension Using dN6P Substrates and Variant TdT Enzyme TdT cysteine variant NTT-1 was used for single strand extension. FIG. 10A shows TdT bound to polyA ssDNA substrate. FIG. 10B shows expression and purification of NTT-1. FIG. 10C shows a schema of a NTT-TIDE.

Figure 11:
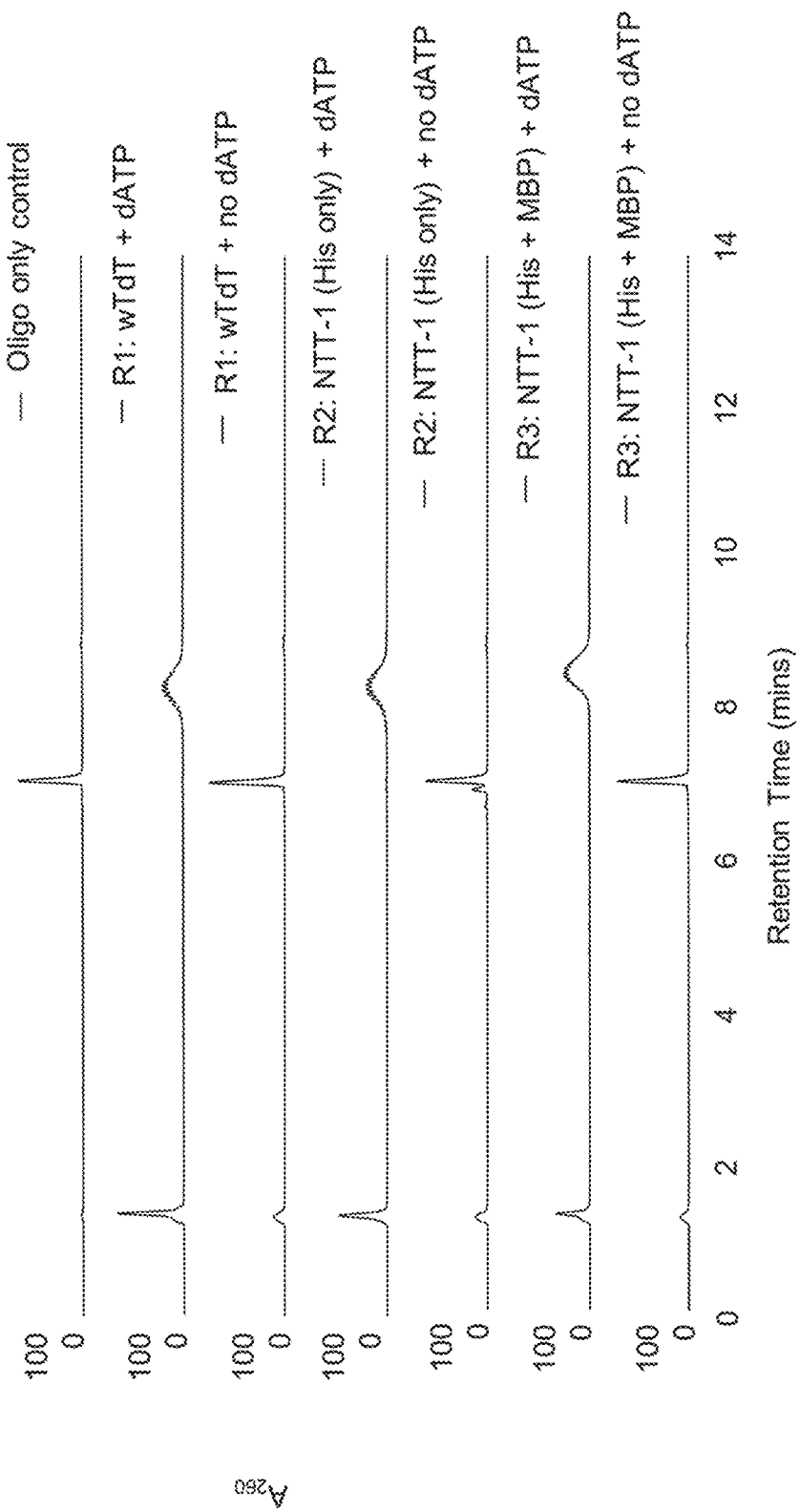
FIG. 11 illustrates extension activity of NTT-1.

Using such NTT-TIDES, NTT-1 was found to exhibit extensions activity (FIG. 11).

Figure 12:
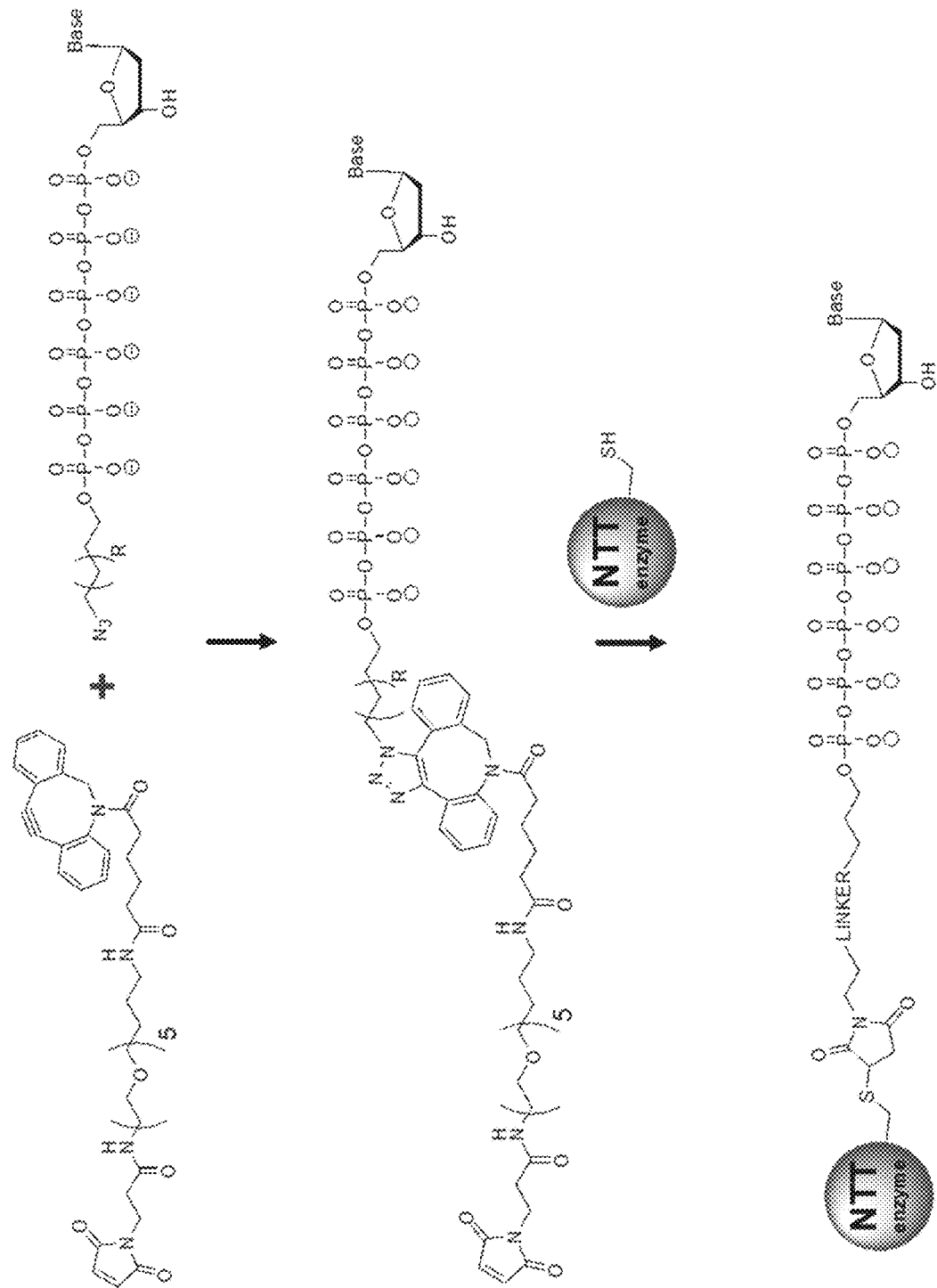
FIG. 12 illustrates a bioconjugation scheme.
Figure 13A:
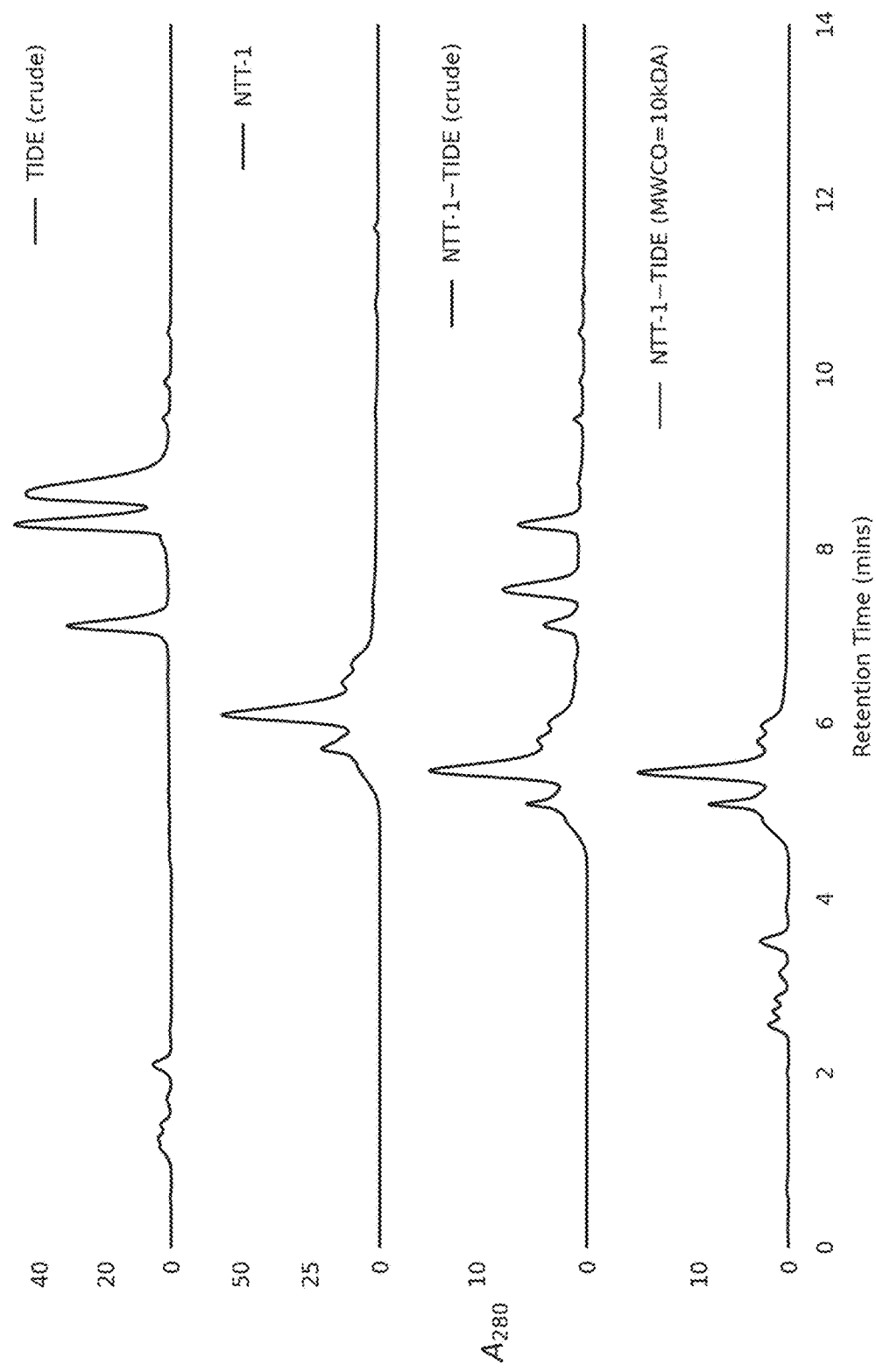
FIGS. 13A-13C illustrate data from bioconjugation.
Figure 13B:
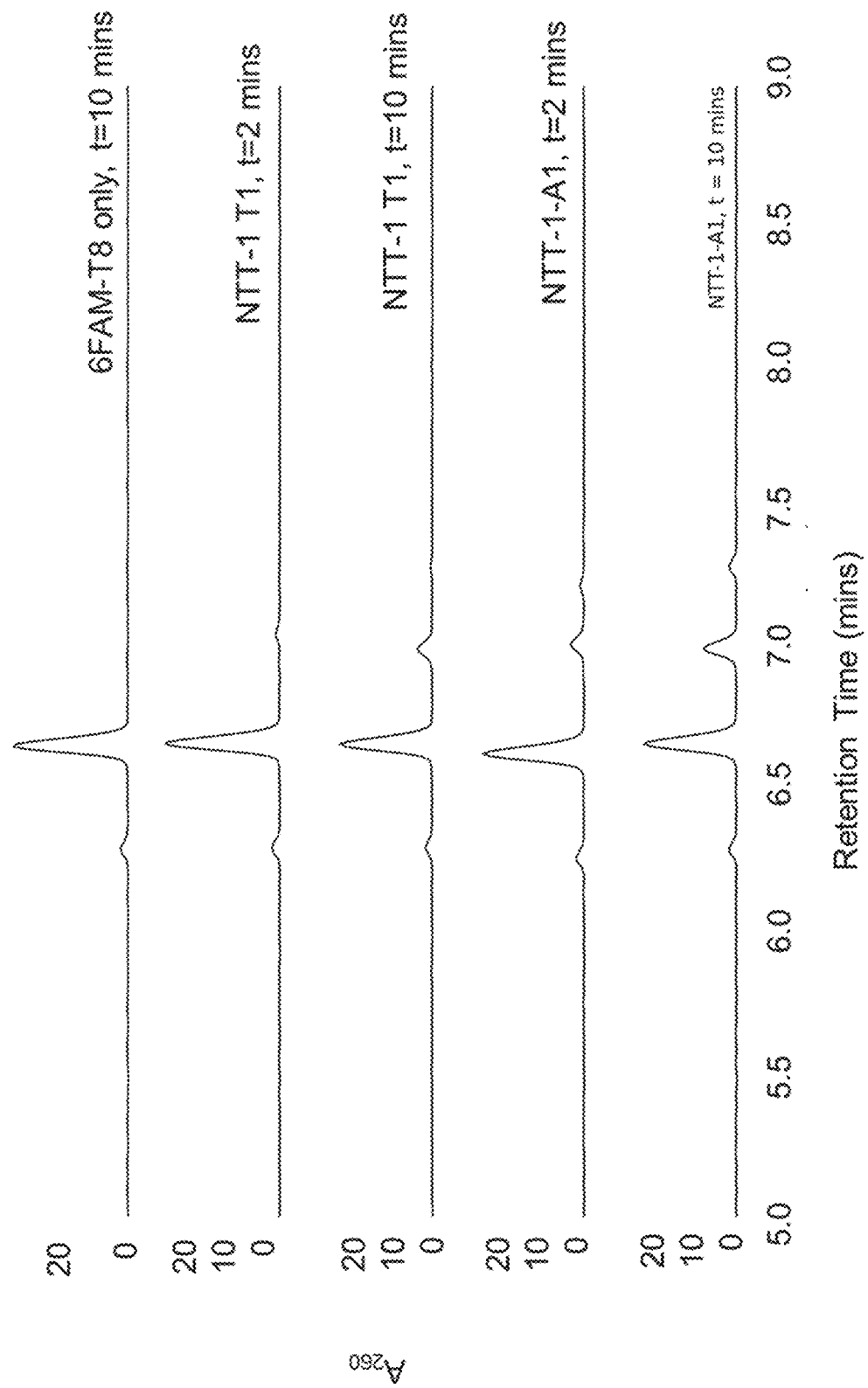
Figure 13C:
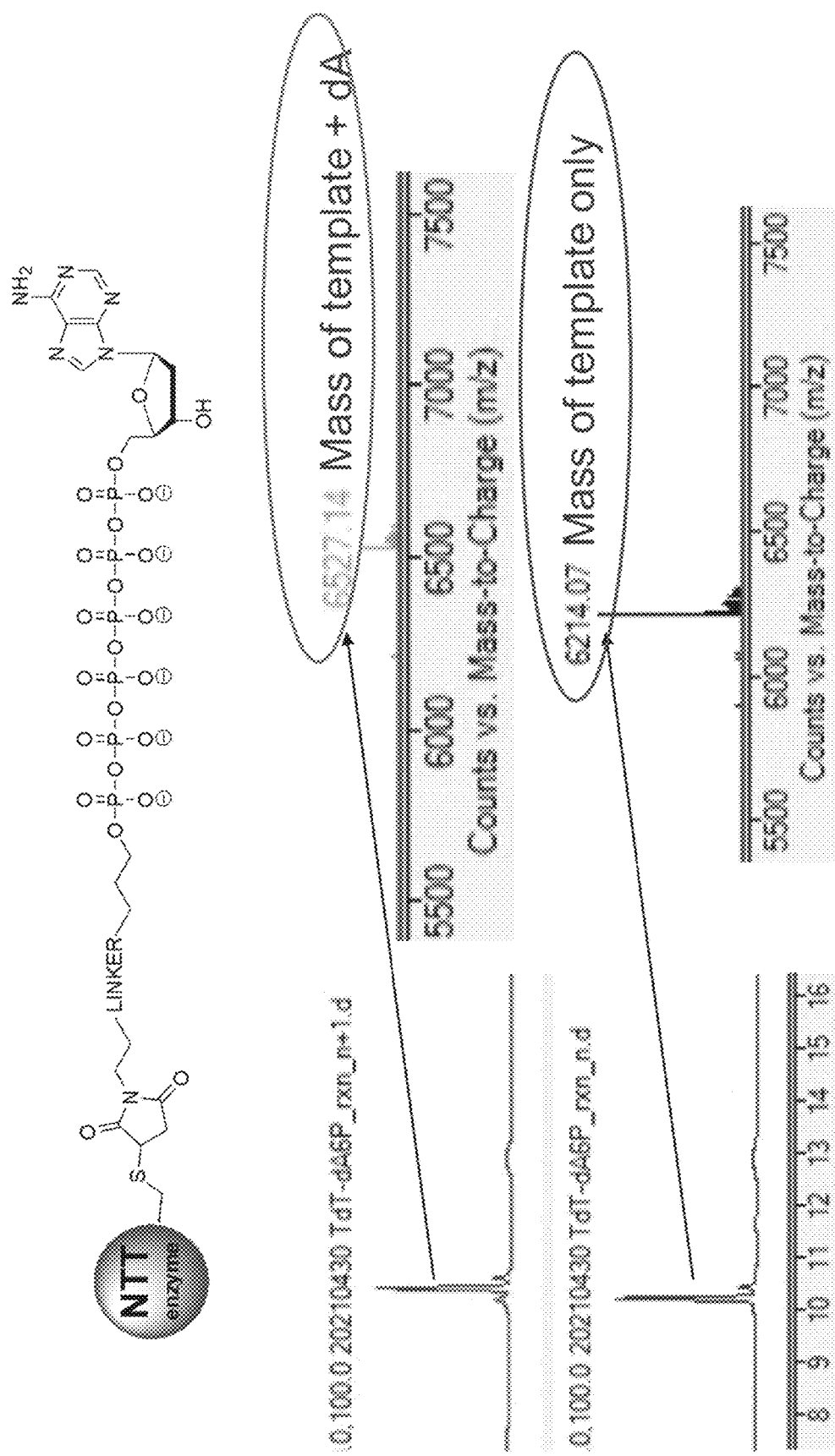

The bioconjugation scheme is seen in FIG. 12 and data from such scheme is seen in FIGS. 13A-13C.

Example 3: Enzymatic Synthesis on a Surface

Enzymatic synthesis was performed on a surface. Briefly, reverse phosphoramidites were used as was diethylamine to gently remove cyanoethyl group, leaving linker attachment in place. dT was also used.

Figure 14:
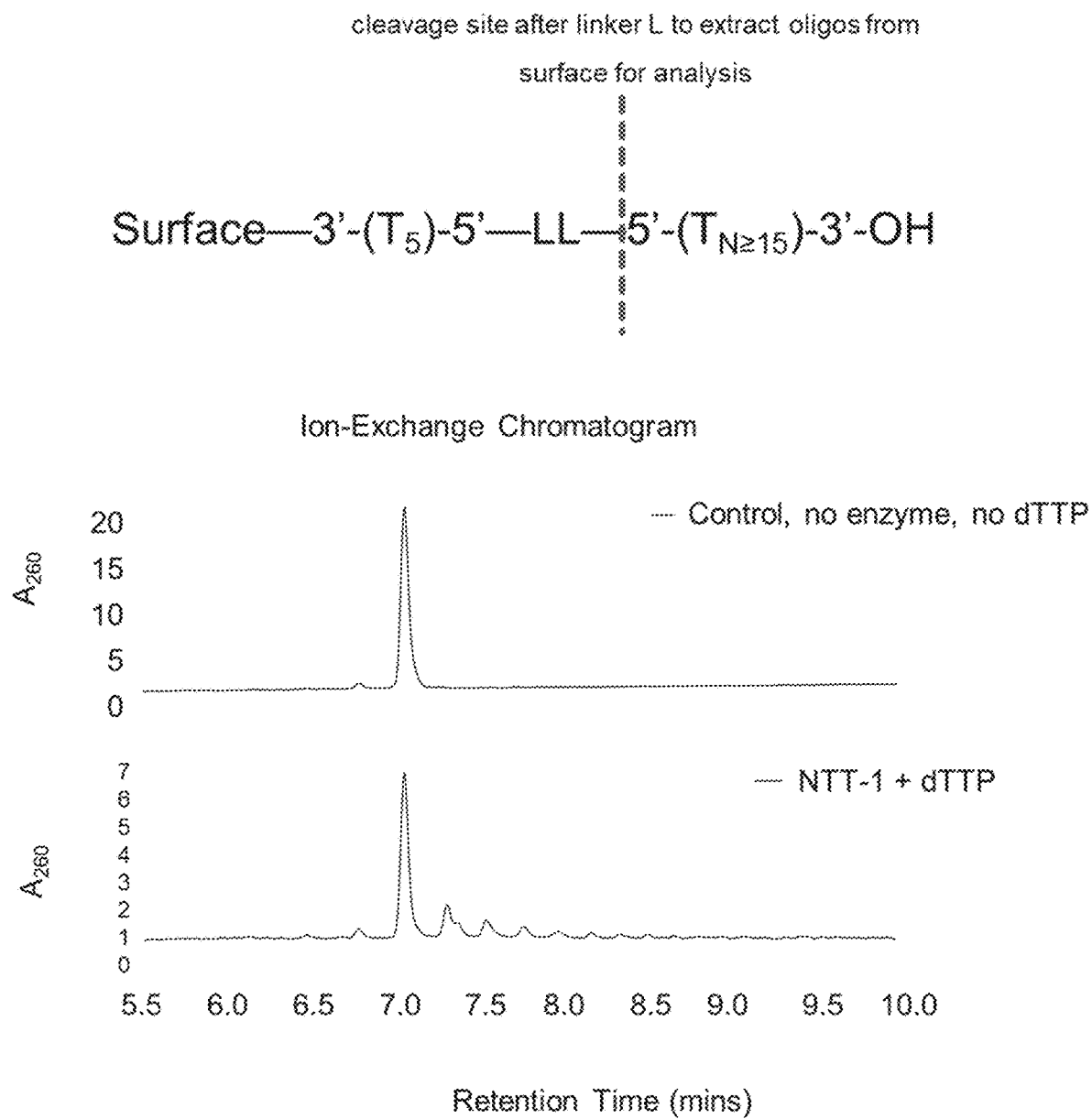
FIG. 14 illustrates data of enzymatic synthesis on a surface.

Data is seen in FIG. 14 that demonstrates that enzymatic synthesis on a surface was observed.

Example 4: Single Strand Chain Extension Using dATPs and dA6Ps

Figure 15A:
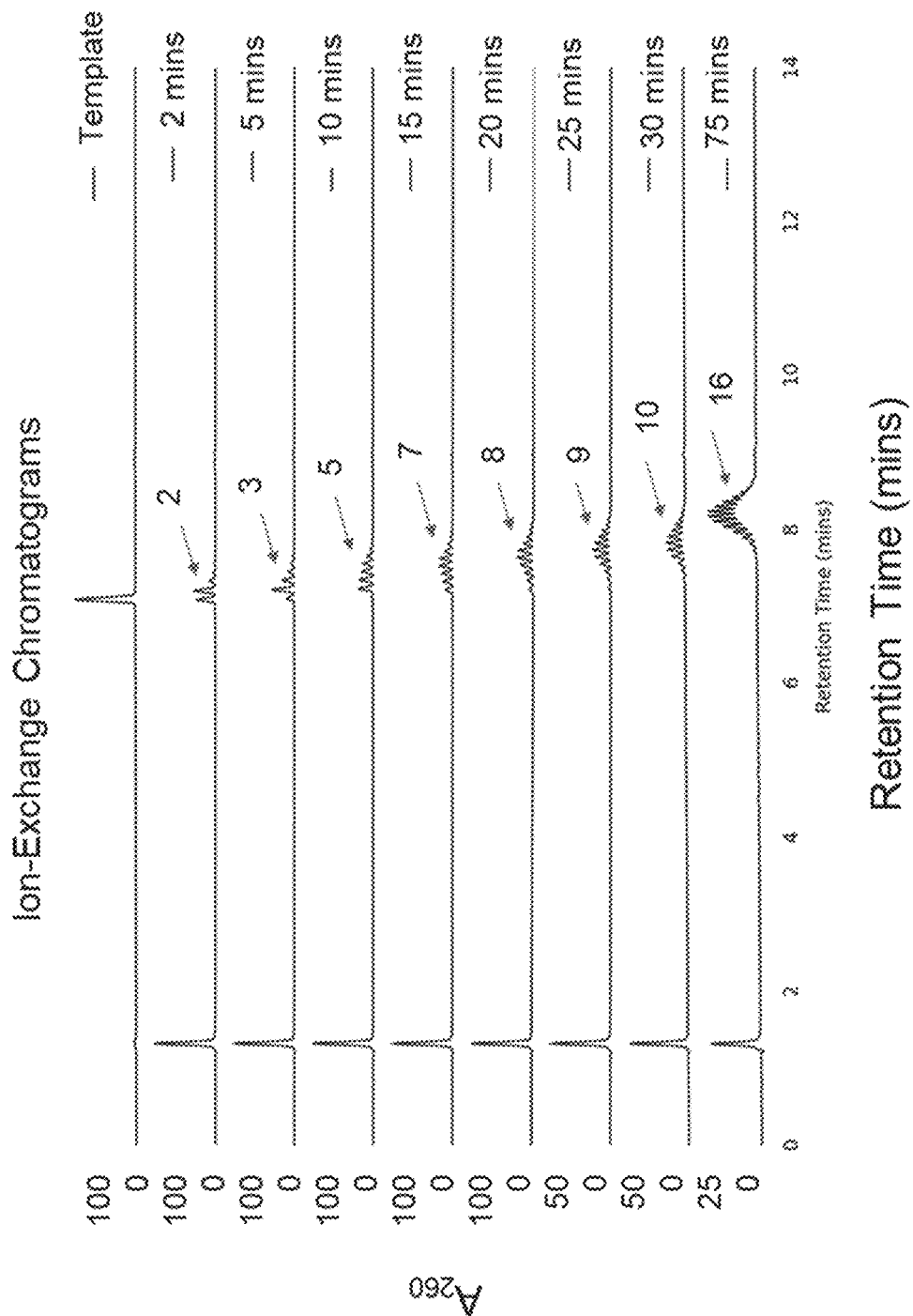
FIGS. 15A-15B illustrate data for extension using dATPs.
Figure 15B:
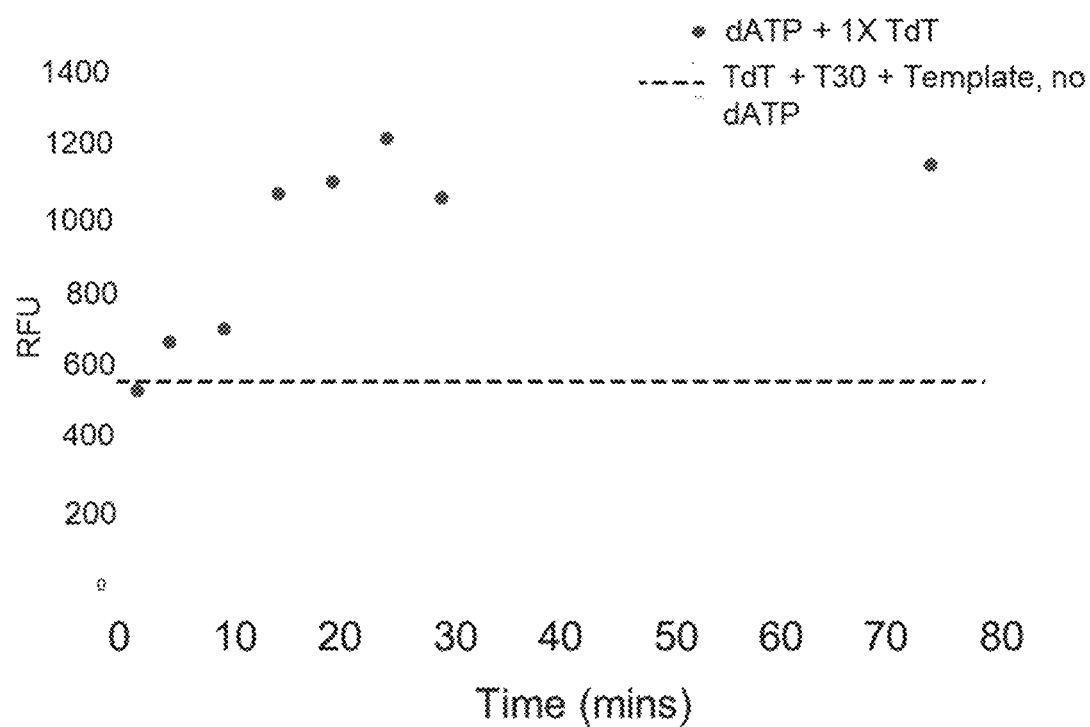
Figure 16A:
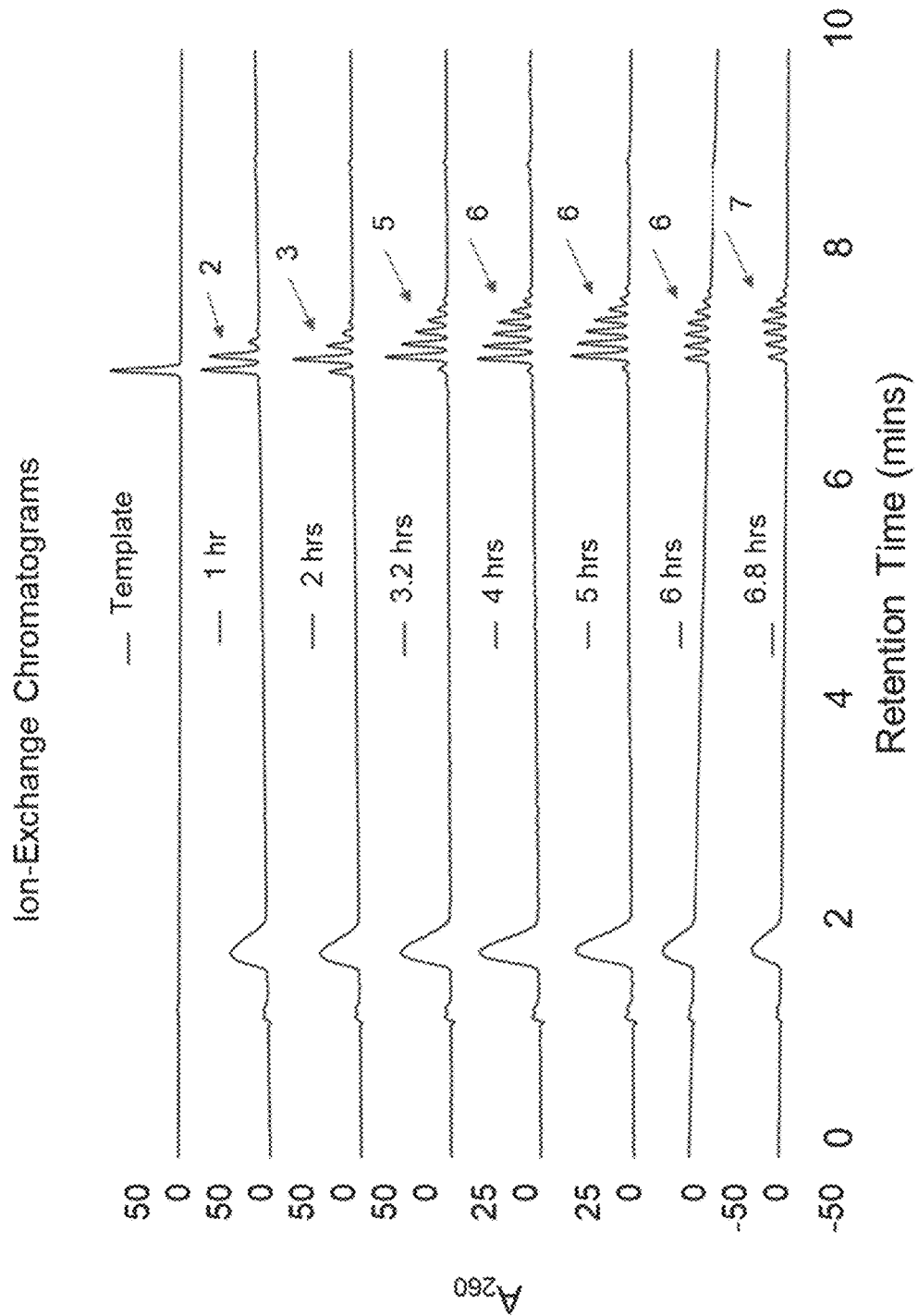
FIGS. 16A-16B illustrate data for extension using dA6Ps.
Figure 16B:
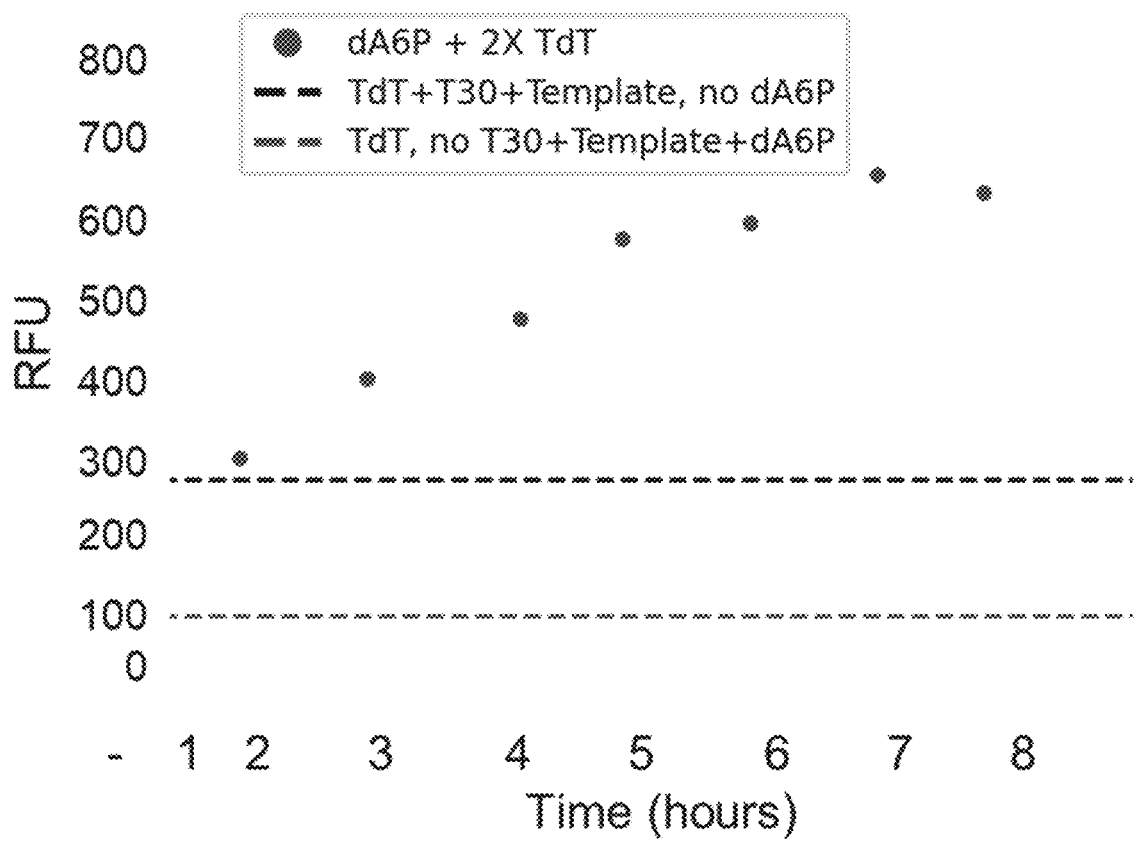

An extension reaction similar to Example 1 was performed. Data for dATPs is seen in FIGS. 15A-15B. Data for dA6Ps is seen in FIGS. 16A-16B.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A composition comprising a complex according to the following formula:

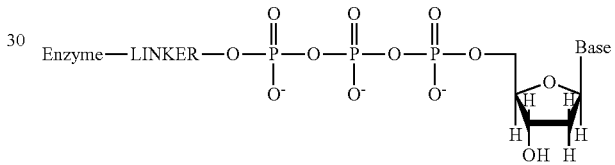

wherein the enzyme comprises TdT.

2. The composition of claim 1, wherein the linker comprises at least one phosphate.

3. The composition of claim 1, wherein the enzyme is attached to the linker via a cysteine.

4. The composition of claim 1, wherein the linker is an acid labile linker, a base labile linker, a pH-sensitive linker, an amine-to-thiol crosslinker, a thiomaleamic acid linker, a photo-cleavable linker, orthonitrobenzyl-based linker, phenacyl linker, alkoxybenzoin linker, chromium arene complex linker, NpSSMpact linker, pivaloylglycol linker, irradiation-cleavable linker, and/or an enzymatically-cleavable linker.

5. The composition of claim 4, wherein the linker is an enzymatically-cleavable linker that is capable of being cleaved using a peptidase or an esterase.

6. The composition of claim 1, wherein the linker is selected from the group consisting of a silyl linker, an alkyl linker, a polyether linker, a polysulfonyl linker, a polysulfoxide linker, an amine-to-thiol cross linker, a thiomaleamic acid linker, and any combination thereof.

7. The composition of claim 1, wherein the enzyme comprises a cysteine mutation.

8. The composition of claim 1, wherein the template independent polymerase comprises at least one amino acid mutation to a surface-accessible amino acid residue.

9. The composition of claim 1, wherein the base is selected from an adenine (A), cytosine (C), guanine (G), thymine (T), uracil (U), or a modified base thereof.

10. The composition of claim 1, further comprising a reversible terminator.

11. A method of synthesizing a polynucleotide, comprising:
(a) contacting a polynucleotide with a composition of claim 1;
(b) extending the polynucleotide by covalent addition of an extension nucleotide onto a 3' hydroxyl of the polynucleotide by the enzyme; and
(c) cleaving the enzyme from the polynucleotide.

12. The method of claim 11, further comprising repeating (a)-(c) to produce an extended polynucleotide.

13. The method of claim 11, wherein the enzyme is cleaved using a peptidase or an esterase.

14. A composition comprising a complex according to the following formula:

A-L-B wherein:
A comprises an enzyme including TdT;
B comprises a nucleotide; and
L comprises a chemical linker that covalently links the enzyme to a terminal phosphate group of the nucleotide, wherein the enzyme is configured to catalyze covalent addition of the nucleotide onto a 3' hydroxyl of a polynucleotide, and subsequent extension of the polynucleotide.

15. The composition of claim 14, wherein the linker comprises at least one phosphate.

16. The composition of claim 14, wherein the linker includes an acid labile linker, a base labile linker, a pH-sensitive linker, an amine-to-thiol crosslinker, a thiomaleamic acid linker, an orthonitrobenzyl-based linker, a phenacyl linker, an alkoxybenzoin linker, a chromium arene complex linker, an NpSSMpact linker, a pivaloylglycol linker, a photo-cleavable linker, an irradiation-cleavable linker, a silyl linker, an alkyl linker, a polyether linker, a polysulfonyl linker, a polysulfoxide linker, an amine-to-thiol crosslinker, a thiomaleamic acid linker, and/or an enzymatically-cleavable linker.

17. The composition of claim 15, wherein the linker is an enzymatically-cleavable linker that is capable of being cleaved using a peptidase or an esterase.

18. The composition of claim 13, wherein the enzyme comprises at least one amino acid mutation to a surface-accessible amino acid residue.

19. The composition of claim 13, wherein the complex further comprises a reversible terminator.

20. The composition of claim 13, wherein the base is includes an adenine, a cytosine, a guanine, a thymine, a uracil, a modified adenine, a modified cytosine, a modified thymine, and/or a modified uracil.

* * * * *

UNITED STATES PATENT AND TRADEMARK OFFICE
CERTIFICATE OF CORRECTION

PATENT NO. : 11,970,697 B2  
APPLICATION NO. : 17/504358  
DATED : April 30, 2024  
INVENTOR(S) : Jeremy Lackey and David Dodd Page 1 of 1

It is certified that error appears in the above-identified patent and that said Letters Patent is hereby corrected as shown below:

On the Title Page

Left Column, Line 9 (assignee paragraph), delete "San Franciso" and insert -- San Francisco --.

In the Claims

In Claim 20, Column 30, Lines 21-22, delete "base is includes" and insert -- base is included --.

Signed and Sealed this  
Ninth Day of July, 2024

Katherine Kelly Vidal  
*Director of the United States Patent and Trademark Office*